US011944436B2

(12) United States Patent
Guerreiro et al.

(10) Patent No.: US 11,944,436 B2
(45) Date of Patent: Apr. 2, 2024

(54) DETERMINING A STRESS LEVEL OF A SMARTPHONE USER BASED ON THE USER'S TOUCH INTERACTIONS AND MOTION SENSOR DATA

(71) Applicant: KOA HEALTH DIGITAL SOLUTIONS S.L.U., Barcelona (ES)

(72) Inventors: Joao Guerreiro, Lisbon (PT); Bartlomiej M. Skorulski, Hospitalet de Llobregat (ES); Aleksandar Matic, Lloret de Mar (ES)

(73) Assignee: Koa Health Digital Solutions S. L. U., Barcelona (ES)

( * ) Notice: Subject to any disclaimer, the term of this patent is extended or adjusted under 35 U.S.C. 154(b) by 211 days.

(21) Appl. No.: 17/227,308

(22) Filed: Apr. 10, 2021

(65) Prior Publication Data

US 2022/0322985 A1 Oct. 13, 2022

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/1114* (2013.01); *A61B 5/6898* (2013.01);
(Continued)

(58) Field of Classification Search
CPC ................. A61B 5/165; G06F 3/0488
(Continued)

(56) References Cited

U.S. PATENT DOCUMENTS 9,521,973 B1 * 12/2016 Beiski .............. A61B 5/168
2012/0289793 A1 11/2012 Jain et al. ............ A61B 5/00
600/301
(Continued)

FOREIGN PATENT DOCUMENTS

JP 2014-094291 A 11/2012

OTHER PUBLICATIONS

Joselli et al., "gRmobile: A Framework for Touch and Accelerometer Gesture Recognition for Mobile Games," Games and Digital Entertainment (SBGAMES), 2009 VIII Brazilian Symposium, IEEE Computer Society, Piscataway, NJ, Oct. 8, 2009, pp. 141-150 XP031685727 (10 pages).
(Continued)

*Primary Examiner* — Fabricio R Murillo Garcia
(74) *Attorney, Agent, or Firm* — Imperium Patent Works; Darien K. Wallace

(57) ABSTRACT

A method for determining a user's stress level is performed by a smartphone app. Touch and motion feature values are generated, the feature values are weighted by regression parameters, and a stress score is generated based on the weighted touch and motion feature values. The touch feature values indicate how the user's finger moves over the smartphone and are generated from touch data points including X positions, Y positions and associated touch timestamp values. The motion feature values indicate movement of the smartphone and are generated from motion data points including X movements, Y movements, Z movements and associated motion timestamp values. The regression parameters are generated using touch and motion data identified by other users as being acquired while those other users were experiencing various perceived levels of stress. The app indicates to the user whether the stress score is higher or lower than a previously generated stress score.

15 Claims, 18 Drawing Sheets

(51) Int. Cl.
  *A61B 5/11*   (2006.01)
  *A61B 90/00*   (2016.01)
  *G06F 3/041*   (2006.01)
  *G06F 3/0488*  (2022.01)

(52) U.S. Cl.
  CPC .......... *A61B 5/7278* (2013.01); *A61B 5/7435* (2013.01); *G06F 3/04146* (2019.05); *G06F 3/0488* (2013.01); *A61B 2090/065* (2016.02); *G06F 2203/04105* (2013.01)

(58) Field of Classification Search
  USPC ...................................................... 455/550.1
  See application file for complete search history.

(56) References Cited

U.S. PATENT DOCUMENTS

| | | | |
|---|---|---|---|
| 2014/0136450 A1 | 5/2014 | Lee | G06N 5/02 |
| 2016/0006941 A1 | 1/2016 | Kim | H04N 5/232 |
| 2017/0071551 A1* | 3/2017 | Jain | A61B 5/4884 |
| 2020/0042687 A1* | 2/2020 | Choi | G06F 3/0488 |
| 2020/0060603 A1* | 2/2020 | Bower | A61B 5/167 |
| 2020/0380882 A1* | 12/2020 | Alailima | A61B 5/4836 |

OTHER PUBLICATIONS

Ruensuk et al., "How Do You Feel Online, " Proceedings of ACM on Interactive, Mobile, Wearable and Ubiquitous Technologies, ACMPUB27, NY, NY, vol. 4, No. 4, Dec. 17, 2020, pp. 1-32, XP058662221 (32 pages).

Sagbas et al., "Stress Detection via Keyboard Typing Behaviors by Using Smartphone Sensors and Machine Learning Techniques," Jour. of Med. Systems, Springer US, NY, vol. 44, No. 4, Feb. 17, 2020, XP037054202 (12 pages).

Wampfler et al., "Affective State Prediction Based on Semi-Supervised Learning from Smartphone Touch Data, " Companion Pub. of 2020 ACM Designing Interactive Sys. Conf., ACMPUB27, Apr. 21, 2020 pp. 1-13, XP058616613 (13 pages).

Extended European Search Report dated Feb. 21, 2022, from the European Patent Office in the related foreign application EP21179548.9 (14 pages).

Ciman et al., "iSenseStress: Assessing stress through human-smartphone interaction analysis," Proceedings of the 9th International Conference on Pervasive Computing Technologies for Healthcare, ICST (Institute for Computer Sciences, Social-Informatics and Telecommunications Engineering) 2015, pp. 84-91 (8 pages).

Ciman et al., "Individuals' stress assessment using human-smartphone interaction analysis," 2016 IEEE, Doi 10.1109/TAFFC. 2016. 2592504 (14 pages).

\* cited by examiner

| TOUCH DATA POINT # | TIME STAMP | x POSITION | y POSITION | DELTA x | DELTA y | PRESSURE | SIZE | MIN RADIUS | MAX RADIUS | ORIENTATION |
|---|---|---|---|---|---|---|---|---|---|---|
| 1 | 1583005689576 | 134.6666565 | 499.6666565 | 0.0000000 | 0.0000000 | 0.0000 | 0 | 10.09796143 | 14.137146000 | -1.570796327 |
| 2 | 1583005689601 | 160.6666565 | 499.0000000 | 26.0000000 | -0.6666565 | 0.4833 | 0 | 10.09796143 | 14.137146000 | -1.570796327 |
| 3 | 1583005689619 | 173.6666565 | 497.0000000 | 13.0000000 | -2.0000000 | 0.4833 | 0 | 10.09796143 | 14.137146000 | -1.570796327 |
| 4 | 1583005689636 | 204.6666565 | 492.6666565 | 31.0000000 | -4.3333435 | 0.4833 | 0 | 10.09796143 | 14.137146000 | -1.570796327 |
| 5 | 1583005689653 | 240.0000000 | 491.3333282 | 35.3333435 | -1.3333282 | 0.4833 | 0 | 10.09796143 | 14.137146000 | -1.570796327 |
| 6 | 1583005689669 | 279.0000000 | 491.3333282 | 39.0000000 | 0.0000000 | 0.4833 | 0 | 10.09796143 | 14.137146000 | -1.570796327 |
| 7 | 1583005689685 | 302.0000000 | 494.3333282 | 23.0000000 | 3.0000000 | 0.4000 | 0 | 6.058776855 | 10.097961430 | -1.570796327 |
| 8 | 1583005689702 | 314.3333282 | 500.0000000 | 12.3333283 | 5.6666718 | 0.3333 | 0 | 6.058776855 | 10.097961430 | -1.570796327 |
| 9 | 1583005689719 | 319.3333282 | 503.3333282 | 5.0000000 | 3.3333282 | 0.3000 | 0 | 6.058776855 | 10.097961430 | -1.570796327 |
| 10 | 1583005689735 | 322.6666565 | 503.6666565 | 3.3333282 | 0.3333282 | 0.2667 | 0 | 6.058776855 | 10.097961430 | -1.570796327 |
| 11 | 1583005689749 | 325.6666565 | 503.6666565 | 3.0000000 | 0.0000000 | 0.2333 | 0 | 6.058776855 | 10.097961430 | -1.570796327 |
| 12 | 1583005689750 | 326.3333282 | 502.3333282 | 0.6666718 | -1.3333282 | 0.2167 | 0 | 6.058776855 | 10.097961430 | -1.570796327 |
| 13 | 1583005689753 | 329.6666565 | 498.6666565 | 3.3333282 | -3.6666718 | 0.2000 | 0 | -2.019592285 | 2.019592285 | -1.570796327 |
| 14 | 1583005689753 | 329.6666565 | 498.6666565 | 0.0000000 | 0.0000000 | 0.2000 | 0 | -2.019592285 | 2.019592285 | -1.570796327 |
| 15 | 1583005690747 | 289.3333282 | 492.0000000 | 0.0000000 | 0.0000000 | 0.0000 | 0 | 6.058776855 | 10.097961430 | -1.570796327 |
| 16 | 1583005690819 | 258.3333282 | 484.6666565 | -31.0000000 | -7.3333435 | 0.2167 | 0 | 6.058776855 | 10.097961430 | -1.570796327 |
| 17 | 1583005690837 | 238.3333282 | 491.0000000 | -20.0000000 | 6.3333435 | 0.2500 | 0 | 6.058776855 | 10.097961430 | -1.570796327 |
| 18 | 1583005690857 | 210.6666565 | 500.6666565 | -27.6666718 | 9.6666565 | 0.2500 | 0 | 6.058776855 | 10.097961430 | -1.570796327 |
| 19 | 1583005690870 | 183.6666565 | 509.6666565 | -27.0000000 | 9.0000000 | 0.2500 | 0 | 6.058776855 | 10.097961430 | -1.570796327 |
| 20 | 1583005690887 | 162.6666565 | 515.6666565 | -21.0000000 | 6.0000000 | 0.2500 | 0 | 6.058776855 | 10.097961430 | -1.570796327 |
| 21 | 1583005690903 | 151.0000000 | 518.6666565 | -11.6666565 | 3.0000000 | 0.2500 | 0 | -2.019592285 | 2.019592285 | -1.570796327 |
| 22 | 1583005690903 | 151.0000000 | 518.6666565 | 0.0000000 | 0.0000000 | 0.2500 | 0 | -2.019592285 | 2.019592285 | -1.570796327 |
| 23 | 1583005692082 | 267.6666565 | 463.6666565 | 0.0000000 | 0.0000000 | 0.3667 | 0 | 6.058776855 | 10.097961430 | -1.570796327 |
| 24 | 1583005692103 | 253.3333282 | 455.6666565 | -14.3333283 | -8.0000000 | 0.4500 | 0 | 6.058776855 | 10.097961430 | -1.570796327 |
| 25 | 1583005692121 | 236.6666565 | 454.0000000 | -16.6666718 | -1.6666565 | 0.4833 | 0 | 6.058776855 | 10.097961430 | -1.570796327 |
| 26 | 1583005692137 | 212.0000000 | 453.0000000 | -24.6666565 | -1.0000000 | 0.4833 | 0 | 10.09796143 | 14.137146000 | -1.570796327 |
| 27 | 1583005692154 | 184.3333282 | 453.3333282 | -27.6666718 | 0.3333282 | 0.4833 | 0 | 10.09796143 | 14.137146000 | -1.570796327 |
| 28 | 1583005692167 | 172.6666565 | 456.3333282 | -11.6666718 | 3.0000000 | 0.4333 | 0 | 10.09796143 | 14.137146000 | -1.570796327 |
| 29 | 1583005692170 | 162.6666565 | 461.3333282 | -10.0000000 | 5.0000000 | 0.3667 | 0 | -2.019592285 | 2.019592285 | -1.570796327 |
| 30 | 1583005692170 | 162.6666565 | 461.3333282 | 0.0000000 | 0.0000000 | 0.3667 | 0 | -2.019592285 | 2.019592285 | -1.570796327 |

FIG. 5A

| TOUCH DATA POINT # | TIME STAMP | x POSITION | y POSITION | DELTA x | DELTA y | PRESSURE | SIZE | MIN RADIUS | MAX RADIUS | ORIENTATION |
|---|---|---|---|---|---|---|---|---|---|---|
| 31 | 1583005693159 | 140.6666565 | 495.3333282 | 0.0000000 | 0.0000000 | 0.0000 | 0 | 6.058776855 | 10.097961430 | -1.570796327 |
| 32 | 1583005693178 | 147.0000000 | 493.6666565 | 6.3333435 | -1.6666718 | 0.2500 | 0 | 6.058776855 | 10.097961430 | -1.570796327 |
| 33 | 1583005693188 | 168.6666565 | 491.0000000 | 21.6666565 | -2.6666565 | 0.2500 | 0 | 6.058776855 | 10.097961430 | -1.570796327 |
| 34 | 1583005693204 | 181.0000000 | 489.0000000 | 12.3333435 | -2.0000000 | 0.2500 | 0 | 6.058776855 | 10.097961430 | -1.570796327 |
| 35 | 1583005693220 | 206.6666565 | 485.0000000 | 25.6666565 | -4.0000000 | 0.2500 | 0 | 6.058776855 | 10.097961430 | -1.570796327 |
| 36 | 1583005693227 | 235.6666565 | 484.3333282 | 29.0000000 | -0.6666718 | 0.2167 | 0 | 6.058776855 | 10.097961430 | -1.570796327 |
| 37 | 1583005693237 | 252.0000000 | 484.3333282 | 16.3333435 | 0.0000000 | 0.2000 | 0 | -2.019592285 | 2.019592285 | -1.570796327 |
| 38 | 1583005693237 | 252.0000000 | 484.3333282 | 0.0000000 | 0.0000000 | 0.2000 | 0 | -2.019592285 | 2.019592285 | -1.570796327 |
| 39 | 1583005693774 | 145.0000000 | 491.0000000 | 0.0000000 | 0.0000000 | 0.1833 | 0 | 10.09796143 | 14.137146000 | -1.570796327 |
| 40 | 1583005693794 | 152.6666565 | 488.3333282 | 7.6666565 | -2.6666718 | 0.3667 | 0 | 10.09796143 | 14.137146000 | -1.570796327 |
| 41 | 1583005693804 | 174.3333282 | 486.0000000 | 21.6666718 | -2.3333282 | 0.3667 | 0 | 10.09796143 | 14.137146000 | -1.570796327 |
| 42 | 1583005693821 | 187.0000000 | 484.6666565 | 12.6666718 | -1.3333435 | 0.3667 | 0 | 10.09796143 | 14.137146000 | -1.570796327 |
| 43 | 1583005693837 | 215.3333282 | 483.0000000 | 28.3333283 | -1.6666565 | 0.3667 | 0 | 10.09796143 | 14.137146000 | -1.570796327 |
| 44 | 1583005693844 | 248.6666565 | 482.3333282 | 33.3333283 | -0.6666718 | 0.3667 | 0 | 10.09796143 | 14.137146000 | -1.570796327 |
| 45 | 1583005693854 | 267.3333282 | 482.3333282 | 18.6666718 | 0.0000000 | 0.3333 | 0 | -2.019592285 | 2.019592285 | -1.570796327 |
| 46 | 1583005693854 | 267.3333282 | 482.3333282 | 0.0000000 | 0.0000000 | 0.3333 | 0 | -2.019592285 | 2.019592285 | -1.570796327 |

FIG. 5B

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 1 | -3.753805542 | 3.869996045 | 8.309722900 | 1583005687989 | 0.000 | 36 | -5.121911621 | 4.184918213 | 7.462899780 | 1583005688337 | 0.348 |
| 2 | -3.805993652 | 3.935641479 | 8.203851318 | 1583005687997 | 0.008 | 37 | -5.111145020 | 4.230676270 | 7.492657471 | 1583005688347 | 0.358 |
| 3 | -3.796722412 | 3.955828857 | 8.047885132 | 1583005688006 | 0.017 | 38 | -5.131781006 | 4.290490723 | 7.505218506 | 1583005688358 | 0.369 |
| 4 | -3.792834473 | 3.963903809 | 7.922274780 | 1583005688017 | 0.028 | 39 | -5.137911987 | 4.311126709 | 7.481442261 | 1583005688367 | 0.378 |
| 5 | -3.833657837 | 3.964801025 | 7.822683716 | 1583005688026 | 0.037 | 40 | -5.126846313 | 4.327276611 | 7.446301270 | 1583005688377 | 0.388 |
| 6 | -3.943865967 | 3.925173950 | 7.750457764 | 1583005688036 | 0.047 | 41 | -5.130584717 | 4.339987183 | 7.387832642 | 1583005688387 | 0.398 |
| 7 | -4.168768311 | 3.766815186 | 7.658193970 | 1583005688046 | 0.057 | 42 | -5.132229614 | 4.393072510 | 7.327569580 | 1583005688397 | 0.408 |
| 8 | -4.243984985 | 3.907528687 | 7.721597290 | 1583005688056 | 0.067 | 43 | -5.110845947 | 4.425820923 | 7.341775513 | 1583005688407 | 0.418 |
| 9 | -4.349557495 | 4.043756104 | 7.746719360 | 1583005688066 | 0.077 | 44 | -5.068826294 | 4.393521118 | 7.311419678 | 1583005688418 | 0.429 |
| 10 | -4.430307007 | 4.078448486 | 7.672100830 | 1583005688077 | 0.088 | 45 | -5.043106079 | 4.361819458 | 7.270596313 | 1583005688427 | 0.438 |
| 11 | -4.573861694 | 4.103271484 | 7.694232178 | 1583005688086 | 0.097 | 46 | -5.067031860 | 4.406381226 | 7.268801880 | 1583005688438 | 0.449 |
| 12 | -4.661340332 | 4.136169434 | 7.690045166 | 1583005688096 | 0.107 | 47 | -5.095742798 | 4.454980469 | 7.221997070 | 1583005688447 | 0.458 |
| 13 | -4.627096558 | 4.114935303 | 7.524060059 | 1583005688107 | 0.118 | 48 | -5.089761353 | 4.441821289 | 7.108200073 | 1583005688457 | 0.468 |
| 14 | -4.563992310 | 4.009661865 | 7.269100952 | 1583005688116 | 0.127 | 49 | -5.108154297 | 4.473672485 | 7.023712158 | 1583005688467 | 0.478 |
| 15 | -4.552627563 | 3.928912354 | 7.082479858 | 1583005688127 | 0.138 | 50 | -5.126696777 | 4.546646118 | 6.981393433 | 1583005688478 | 0.489 |
| 16 | -4.705902100 | 3.949847412 | 6.989767456 | 1583005688136 | 0.147 | 51 | -5.121762085 | 4.577301025 | 6.887036133 | 1583005688488 | 0.499 |
| 17 | -4.944561768 | 4.050083374 | 7.022515869 | 1583005688146 | 0.157 | 52 | -5.118472290 | 4.609600830 | 6.808081055 | 1583005688498 | 0.509 |
| 18 | -5.110696411 | 4.087121582 | 7.163229370 | 1583005688157 | 0.168 | 53 | -5.120266724 | 4.680331421 | 6.732415771 | 1583005688508 | 0.519 |
| 19 | -5.330963135 | 4.204058838 | 6.997991943 | 1583005688167 | 0.178 | 54 | -5.063293457 | 4.720108032 | 6.636413574 | 1583005688518 | 0.529 |
| 20 | -5.367898560 | 4.303500366 | 6.881802368 | 1583005688177 | 0.188 | 55 | -4.962655640 | 4.694238281 | 6.563290405 | 1583005688528 | 0.539 |
| 21 | -5.273690796 | 4.261032104 | 6.905429077 | 1583005688187 | 0.198 | 56 | -4.930804443 | 4.633975220 | 6.592001343 | 1583005688538 | 0.549 |
| 22 | -5.176193237 | 4.145141602 | 6.887036133 | 1583005688197 | 0.208 | 57 | -4.994357300 | 4.596890259 | 6.615328979 | 1583005688548 | 0.559 |
| 23 | -5.078247070 | 4.070971680 | 6.827969360 | 1583005688207 | 0.218 | 58 | -5.160491943 | 4.515542603 | 6.661834717 | 1583005688559 | 0.570 |
| 24 | -5.051330566 | 4.058709717 | 6.849801636 | 1583005688218 | 0.229 | 59 | -5.351748657 | 4.386642456 | 6.872232056 | 1583005688568 | 0.579 |
| 25 | -5.078845215 | 4.100131226 | 6.925915527 | 1583005688227 | 0.238 | 60 | -5.537771606 | 4.271948242 | 7.158892822 | 1583005688579 | 0.590 |
| 26 | -5.122210693 | 4.106561279 | 6.992758179 | 1583005688237 | 0.248 | 61 | -5.665325928 | 4.173852539 | 7.452133179 | 1583005688588 | 0.599 |
| 27 | -5.174847412 | 4.104916382 | 7.043002319 | 1583005688247 | 0.258 | 62 | -5.457470703 | 4.047793579 | 7.405477905 | 1583005688599 | 0.610 |
| 28 | -5.367300415 | 3.963455200 | 7.031936646 | 1583005688257 | 0.268 | 63 | -5.269802856 | 4.026409912 | 7.262072754 | 1583005688608 | 0.619 |
| 29 | -5.367300415 | 4.065139771 | 7.293026733 | 1583005688267 | 0.278 | 64 | -5.225390625 | 4.068878174 | 7.192089844 | 1583005688619 | 0.630 |
| 30 | -5.266513062 | 4.238751221 | 7.483236694 | 1583005688277 | 0.288 | 65 | -5.171856689 | 4.069625854 | 7.179080200 | 1583005688628 | 0.639 |
| 31 | -5.186810303 | 4.214526367 | 7.508807373 | 1583005688291 | 0.302 | 66 | -5.160192871 | 4.065139771 | 7.205847168 | 1583005688638 | 0.649 |
| 32 | -5.232119751 | 4.061999512 | 7.553967285 | 1583005688297 | 0.308 | 67 | -5.158398438 | 4.071270752 | 7.280764771 | 1583005688648 | 0.659 |
| 33 | -5.244680786 | 4.039569092 | 7.680474854 | 1583005688307 | 0.318 | 68 | -5.163183594 | 4.131533813 | 7.393515015 | 1583005688658 | 0.669 |
| 34 | -5.207446289 | 4.157702637 | 7.739691162 | 1583005688318 | 0.329 | 69 | -5.176342773 | 4.181179810 | 7.370187378 | 1583005688668 | 0.679 |
| 35 | -5.154959106 | 4.192694092 | 7.589706421 | 1583005688327 | 0.338 | 70 | -5.188903809 | 4.241592407 | 7.235903931 | 1583005688678 | 0.689 |

FIG. 6A

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 71 | -5.200268555 | 4.342529297 | 7.084722900 | 1583005688689 | 0.700 | 106 | -5.131481934 | 4.565936279 | 7.216912842 | 1583005689040 | 1.051 |
| 72 | -5.201315308 | 4.446307373 | 6.999487305 | 1583005688699 | 0.710 | 107 | -5.156903076 | 4.666424561 | 7.213473511 | 1583005689049 | 1.060 |
| 73 | -5.178436279 | 4.564291382 | 6.905578613 | 1583005688709 | 0.720 | 108 | -5.153314209 | 4.670761108 | 7.095190430 | 1583005689060 | 1.071 |
| 74 | -5.148678589 | 4.657751465 | 6.870736694 | 1583005688719 | 0.730 | 109 | -5.123855591 | 4.644293213 | 7.038665771 | 1583005689070 | 1.081 |
| 75 | -5.072714233 | 4.684518433 | 6.846661377 | 1583005688729 | 0.740 | 110 | -5.106060791 | 4.654760742 | 7.011898804 | 1583005689080 | 1.091 |
| 76 | -5.003179932 | 4.660592651 | 6.901989746 | 1583005688739 | 0.750 | 111 | -5.089910889 | 4.656256104 | 6.948196411 | 1583005689090 | 1.101 |
| 77 | -5.018582153 | 4.652069092 | 7.025506592 | 1583005688749 | 0.760 | 112 | -5.121612549 | 4.663284302 | 6.916943359 | 1583005689100 | 1.111 |
| 78 | -5.000637817 | 4.625451660 | 7.168612671 | 1583005688759 | 0.770 | 113 | -5.189651489 | 4.700668335 | 6.898101807 | 1583005689110 | 1.121 |
| 79 | -4.965496826 | 4.578796387 | 7.251904297 | 1583005688769 | 0.780 | 114 | -5.255746460 | 4.780221558 | 6.888082886 | 1583005689120 | 1.131 |
| 80 | -4.992562866 | 4.555468750 | 7.286596680 | 1583005688779 | 0.790 | 115 | -5.281167603 | 4.833456421 | 6.882550049 | 1583005689130 | 1.141 |
| 81 | -5.055218506 | 4.556665039 | 7.290634155 | 1583005688789 | 0.800 | 116 | -5.235110474 | 4.814315796 | 6.808679199 | 1583005689140 | 1.151 |
| 82 | -5.076751709 | 4.565188599 | 7.240988159 | 1583005688799 | 0.810 | 117 | -5.197726440 | 4.807586670 | 6.752005005 | 1583005689150 | 1.161 |
| 83 | -5.068975830 | 4.563244629 | 7.175939941 | 1583005688809 | 0.820 | 118 | -5.186062622 | 4.813269043 | 6.735256958 | 1583005689160 | 1.171 |
| 84 | -5.053125000 | 4.541711426 | 7.150070190 | 1583005688819 | 0.830 | 119 | -5.186212158 | 4.838989258 | 6.706396484 | 1583005689170 | 1.181 |
| 85 | -5.053424072 | 4.547244263 | 7.127789307 | 1583005688829 | 0.840 | 120 | -5.126098633 | 4.805941772 | 6.739144897 | 1583005689180 | 1.191 |
| 86 | -5.093051147 | 4.590609741 | 7.001580811 | 1583005688839 | 0.850 | 121 | -5.132379150 | 4.801156616 | 6.726882935 | 1583005689190 | 1.201 |
| 87 | -5.118023682 | 4.667770386 | 6.825427246 | 1583005688849 | 0.860 | 122 | -5.160192871 | 4.874279785 | 6.695330811 | 1583005689200 | 1.211 |
| 88 | -5.094995117 | 4.684069824 | 6.769351196 | 1583005688859 | 0.870 | 123 | -5.165127563 | 4.855587769 | 6.742135620 | 1583005689210 | 1.221 |
| 89 | -5.057461548 | 4.647732544 | 6.824230957 | 1583005688869 | 0.880 | 124 | -5.176193237 | 4.869644165 | 6.714471436 | 1583005689221 | 1.232 |
| 90 | -5.079293823 | 4.607208252 | 6.944757080 | 1583005688879 | 0.890 | 125 | -5.163034058 | 4.849905396 | 6.691891479 | 1583005689230 | 1.241 |
| 91 | -5.158099365 | 4.593450928 | 7.097433472 | 1583005688889 | 0.900 | 126 | -5.133425903 | 4.803250122 | 6.673498535 | 1583005689240 | 1.251 |
| 92 | -5.208642578 | 4.550085449 | 7.115527344 | 1583005688899 | 0.910 | 127 | -5.121762085 | 4.757641602 | 6.675891113 | 1583005689250 | 1.261 |
| 93 | -5.256643677 | 4.510159302 | 7.120761108 | 1583005688909 | 0.920 | 128 | -5.131631470 | 4.760632324 | 6.710433960 | 1583005689260 | 1.271 |
| 94 | -5.281466675 | 4.475466919 | 7.146331787 | 1583005688919 | 0.930 | 129 | -5.141949463 | 4.788745117 | 6.725537109 | 1583005689270 | 1.281 |
| 95 | -5.287298584 | 4.454980469 | 7.119415283 | 1583005688929 | 0.940 | 130 | -5.132080078 | 4.792184448 | 6.753051758 | 1583005689280 | 1.291 |
| 96 | -5.272045898 | 4.487280273 | 7.039712524 | 1583005688939 | 0.950 | 131 | -5.127444458 | 4.817007446 | 6.712527466 | 1583005689290 | 1.301 |
| 97 | -5.270700073 | 4.527206421 | 6.996047974 | 1583005688949 | 0.960 | 132 | -5.204156494 | 4.869494629 | 6.721948242 | 1583005689300 | 1.311 |
| 98 | -5.240045166 | 4.543206787 | 7.001281738 | 1583005688959 | 0.970 | 133 | -5.257241821 | 4.920635986 | 6.848455811 | 1583005689310 | 1.321 |
| 99 | -5.233166504 | 4.519729614 | 6.995898438 | 1583005688969 | 0.980 | 134 | -5.222998047 | 4.950244141 | 6.909466553 | 1583005689321 | 1.332 |
| 100 | -5.249465942 | 4.486682129 | 7.002478027 | 1583005688979 | 0.990 | 135 | -5.171557617 | 4.912411499 | 6.863259888 | 1583005689330 | 1.341 |
| 101 | -5.336047363 | 4.370941162 | 6.983187866 | 1583005688989 | 1.000 | 136 | -5.122061157 | 4.851101685 | 6.843072510 | 1583005689341 | 1.352 |
| 102 | -5.291784668 | 4.521673584 | 7.174295044 | 1583005689000 | 1.011 | 137 | -5.105612183 | 4.768258667 | 6.808230591 | 1583005689350 | 1.361 |
| 103 | -5.250662231 | 4.606161499 | 7.300354004 | 1583005689009 | 1.020 | 138 | -5.207894897 | 4.738650513 | 6.743032837 | 1583005689361 | 1.372 |
| 104 | -5.152117920 | 4.531094360 | 7.210781860 | 1583005689020 | 1.031 | 139 | -5.294476318 | 4.729229736 | 6.763369751 | 1583005689371 | 1.382 |
| 105 | -5.124603271 | 4.477410889 | 7.166668701 | 1583005689030 | 1.041 | 140 | -5.323187256 | 4.725640869 | 6.809725952 | 1583005689381 | 1.392 |

FIG. 6B

| MOTION DATA POINT # | x | y | z | TIME STAMP | TIME ELAPSED |
|---|---|---|---|---|---|
| 141 | -5.260083008 | 4.696481323 | 6.794921875 | 1583005689391 | 1.402 |
| 142 | -5.190548706 | 4.732968140 | 6.746621704 | 1583005689401 | 1.412 |
| 143 | -5.274288940 | 4.749118042 | 6.620114136 | 1583005689411 | 1.422 |
| 144 | -5.388684082 | 4.737304688 | 6.503027344 | 1583005689421 | 1.432 |
| 145 | -5.556762695 | 4.796520996 | 6.550878906 | 1583005689431 | 1.442 |
| 146 | -5.670709229 | 4.741491699 | 6.526953125 | 1583005689441 | 1.452 |
| 147 | -5.874526978 | 4.731323242 | 6.474316406 | 1583005689451 | 1.462 |
| 148 | -6.084176636 | 4.742538452 | 6.468634033 | 1583005689461 | 1.472 |
| 149 | -6.248217773 | 4.740145874 | 6.426464844 | 1583005689471 | 1.482 |
| 150 | -6.380258179 | 4.817456055 | 6.357977295 | 1583005689481 | 1.492 |
| 151 | -6.415399170 | 4.877569580 | 6.313415527 | 1583005689491 | 1.502 |
| 152 | -6.321340942 | 4.933496094 | 6.203207397 | 1583005689501 | 1.512 |
| 153 | -6.198571777 | 4.996151733 | 6.062344360 | 1583005689511 | 1.522 |
| 154 | -6.156701660 | 5.055966187 | 5.857629395 | 1583005689521 | 1.532 |
| 155 | -6.130233765 | 5.179034424 | 5.685662842 | 1583005689531 | 1.542 |
| 156 | -6.084176636 | 5.297167969 | 5.595941162 | 1583005689541 | 1.552 |
| 157 | -5.993557739 | 5.349655151 | 5.596987915 | 1583005689551 | 1.562 |
| 158 | -5.995800781 | 5.328271484 | 5.577099609 | 1583005689561 | 1.572 |
| 159 | -5.967987061 | 5.250662231 | 5.448797607 | 1583005689571 | 1.582 |
| 160 | -6.224740601 | 5.363562012 | 5.230175781 | 1583005689581 | 1.592 |
| 161 | -6.492559814 | 5.345169067 | 5.260531616 | 1583005689591 | 1.602 |
| 162 | -6.044699097 | 5.430703735 | 5.370141602 | 1583005689601 | 1.612 |
| 163 | -5.506817627 | 5.331262207 | 5.569024658 | 1583005689611 | 1.622 |
| 164 | -5.347860718 | 5.069573975 | 6.269900513 | 1583005689621 | 1.632 |
| 165 | -5.341879272 | 4.774688721 | 6.875764282 | 1583005689631 | 1.642 |
| 166 | -5.460610962 | 4.560253906 | 7.410113525 | 1583005689641 | 1.652 |
| 167 | -5.508013916 | 4.575057983 | 7.939321899 | 1583005689651 | 1.662 |
| 168 | -5.280868530 | 4.700668335 | 8.127139282 | 1583005689661 | 1.672 |
| 169 | -4.996749878 | 4.591207886 | 7.840628052 | 1583005689671 | 1.682 |
| 170 | -4.970281982 | 4.290789795 | 7.667764282 | 1583005689681 | 1.692 |
| 171 | -5.185015869 | 4.194189453 | 7.714718628 | 1583005689691 | 1.702 |
| 172 | -5.296868896 | 4.375427246 | 7.368243408 | 1583005689702 | 1.713 |
| 173 | -5.327075195 | 4.616180420 | 6.802548218 | 1583005689711 | 1.722 |
| 174 | -5.329168701 | 4.867102051 | 6.306536865 | 1583005689721 | 1.732 |
| 175 | -5.244237744 | 5.031890869 | 5.916247559 | 1583005689731 | 1.742 |
| 176 | -5.099630737 | 5.101275635 | 5.748168945 | 1583005689743 | 1.754 |
| 177 | -5.031143188 | 5.174847412 | 5.752804565 | 1583005689753 | 1.764 |
| 178 | -5.056863403 | 5.277279663 | 5.861965942 | 1583005689761 | 1.772 |
| 179 | -5.100527954 | 5.356085205 | 6.035128784 | 1583005689771 | 1.782 |
| 180 | -5.157650757 | 5.384945679 | 6.222796631 | 1583005689781 | 1.792 |
| 181 | -5.172903442 | 5.301205444 | 6.417193604 | 1583005689791 | 1.802 |
| 182 | -5.205801392 | 5.190698242 | 6.630133057 | 1583005689803 | 1.814 |
| 183 | -5.245278931 | 5.069723511 | 6.775033569 | 1583005689811 | 1.822 |
| 184 | -5.268905640 | 4.954730225 | 6.784304810 | 1583005689821 | 1.832 |
| 185 | -5.304046631 | 4.908822632 | 6.765762329 | 1583005689831 | 1.842 |
| 186 | -5.339187622 | 4.914804077 | 6.706546021 | 1583005689842 | 1.853 |
| 187 | -5.354141235 | 4.954132080 | 6.607852173 | 1583005689853 | 1.864 |
| 188 | -5.300756836 | 4.994357300 | 6.479849243 | 1583005689862 | 1.873 |
| 189 | -5.293579102 | 5.044302368 | 6.413604736 | 1583005689875 | 1.886 |
| 190 | -5.322589111 | 5.095443726 | 6.428259277 | 1583005689882 | 1.893 |
| 191 | -5.326327515 | 5.135968018 | 6.462802124 | 1583005689891 | 1.902 |
| 192 | -5.284906006 | 5.135818481 | 6.460858154 | 1583005689902 | 1.913 |
| 193 | -5.275335693 | 5.124902344 | 6.538916016 | 1583005689912 | 1.923 |
| 194 | -5.284906006 | 5.101574707 | 6.651666260 | 1583005689922 | 1.933 |
| 195 | -5.287448120 | 5.072714233 | 6.629385376 | 1583005689932 | 1.943 |
| 196 | -5.264270020 | 5.056265259 | 6.555364990 | 1583005689942 | 1.953 |
| 197 | -5.206399536 | 5.041461182 | 6.550729370 | 1583005689952 | 1.963 |
| 198 | -5.188006592 | 5.032788086 | 6.605758667 | 1583005689962 | 1.973 |
| 199 | -5.195034790 | 5.025161743 | 6.689498901 | 1583005689972 | 1.983 |
| 200 | -5.198922729 | 5.006619263 | 6.727481079 | 1583005689982 | 1.993 |
| 201 | -5.181875610 | 4.997497559 | 6.685012817 | 1583005689992 | 2.003 |
| 202 | -5.153912354 | 5.027105713 | 6.562243652 | 1583005690002 | 2.013 |
| 203 | -5.194885254 | 5.060601807 | 6.505718994 | 1583005690012 | 2.023 |
| 204 | -5.297728638 | 5.098284912 | 6.509158325 | 1583005690022 | 2.033 |
| 205 | -5.343225098 | 5.120117188 | 6.521569824 | 1583005690032 | 2.043 |
| 206 | -5.310028076 | 5.125051880 | 6.514093018 | 1583005690042 | 2.053 |
| 207 | -5.241989136 | 5.121612549 | 6.545346069 | 1583005690052 | 2.063 |
| 208 | -5.207296753 | 5.107705688 | 6.565682983 | 1583005690062 | 2.073 |
| 209 | -5.226736450 | 5.085723877 | 6.613235474 | 1583005690072 | 2.083 |
| 210 | -5.241091919 | 5.078546143 | 6.616076660 | 1583005690083 | 2.094 |

FIG. 6C

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 211 | -5.206997681 | 5.051480103 | 6.554617310 | 1583005690092 | 2.103 | 246 | -5.253802490 | 5.034582520 | 6.847558594 | 1583005690444 | 2.455 |
| 212 | -5.177688599 | 5.047143555 | 6.541159058 | 1583005690103 | 2.114 | 247 | -5.241839600 | 4.996450806 | 6.774884033 | 1583005690454 | 2.465 |
| 213 | -5.160491943 | 5.033535767 | 6.551776123 | 1583005690113 | 2.124 | 248 | -5.223745728 | 4.999740601 | 6.696676636 | 1583005690464 | 2.475 |
| 214 | -5.175445557 | 5.020675659 | 6.652413940 | 1583005690123 | 2.134 | 249 | -5.191146851 | 5.007067871 | 6.657946777 | 1583005690474 | 2.485 |
| 215 | -5.178137207 | 5.022021484 | 6.741836548 | 1583005690133 | 2.144 | 250 | -5.119070435 | 4.993310547 | 6.631927490 | 1583005690484 | 2.495 |
| 216 | -5.167669678 | 5.027703857 | 6.717013550 | 1583005690143 | 2.154 | 251 | -5.064639282 | 4.997740600 | 6.617123413 | 1583005690494 | 2.505 |
| 217 | -5.126397705 | 5.011105347 | 6.695928955 | 1583005690153 | 2.164 | 252 | -5.050582886 | 5.028750610 | 6.604459595 | 1583005690504 | 2.515 |
| 218 | -5.078994751 | 5.005572510 | 6.671405029 | 1583005690163 | 2.174 | 253 | -5.035031128 | 5.032489014 | 6.586318970 | 1583005690514 | 2.525 |
| 219 | -5.124005127 | 5.033236694 | 6.631329346 | 1583005690173 | 2.184 | 254 | -5.041162109 | 5.011703491 | 6.573608398 | 1583005690524 | 2.535 |
| 220 | -5.225540161 | 5.094247437 | 6.550579834 | 1583005690183 | 2.194 | 255 | -5.085873413 | 5.018731689 | 6.588262939 | 1583005690535 | 2.546 |
| 221 | -5.309729004 | 5.127743530 | 6.507064819 | 1583005690193 | 2.204 | 256 | -5.147482300 | 5.020077515 | 6.579888916 | 1583005690544 | 2.555 |
| 222 | -5.286999512 | 5.096789551 | 6.532485962 | 1583005690203 | 2.214 | 257 | -5.179183960 | 5.001983643 | 6.608001709 | 1583005690554 | 2.565 |
| 223 | -5.253802490 | 5.059405518 | 6.575851440 | 1583005690213 | 2.224 | 258 | -5.193240356 | 5.009909058 | 6.687854004 | 1583005690564 | 2.575 |
| 224 | -5.263073730 | 5.037274170 | 6.659591675 | 1583005690224 | 2.235 | 259 | -5.224044800 | 5.048638916 | 6.701760864 | 1583005690574 | 2.585 |
| 225 | -5.266064453 | 5.053274536 | 6.669161987 | 1583005690233 | 2.244 | 260 | -5.189053345 | 5.032489014 | 6.676339722 | 1583005690584 | 2.595 |
| 226 | -5.256344604 | 5.057760620 | 6.645684814 | 1583005690243 | 2.254 | 261 | -5.133575439 | 5.015591431 | 6.653311157 | 1583005690594 | 2.605 |
| 227 | -5.216867065 | 5.057910156 | 6.627890015 | 1583005690253 | 2.264 | 262 | -5.119070435 | 5.012899780 | 6.658843994 | 1583005690604 | 2.615 |
| 228 | -5.184567261 | 5.025759888 | 6.667218018 | 1583005690264 | 2.275 | 263 | -5.126995850 | 5.005572510 | 6.709237671 | 1583005690614 | 2.625 |
| 229 | -5.181174683 | 5.008413696 | 6.700363647 | 1583005690273 | 2.284 | 264 | -5.136267090 | 5.001235962 | 6.773837280 | 1583005690624 | 2.635 |
| 230 | -5.198623657 | 5.012301636 | 6.693835449 | 1583005690283 | 2.294 | 265 | -5.152566528 | 4.982244873 | 6.814511108 | 1583005690634 | 2.645 |
| 231 | -5.247372437 | 4.985983276 | 6.721649170 | 1583005690293 | 2.304 | 266 | -5.181277466 | 4.955178833 | 6.805389404 | 1583005690644 | 2.655 |
| 232 | -5.341430664 | 4.965197754 | 6.747518921 | 1583005690303 | 2.314 | 267 | -5.212530518 | 4.943066406 | 6.743331909 | 1583005690654 | 2.665 |
| 233 | -5.429806519 | 4.996450806 | 6.701013184 | 1583005690313 | 2.324 | 268 | -5.229129028 | 4.920486450 | 6.691741943 | 1583005690664 | 2.675 |
| 234 | -5.439825439 | 4.991366577 | 6.699667358 | 1583005690323 | 2.334 | 269 | -5.233166504 | 4.923178101 | 6.697723389 | 1583005690674 | 2.685 |
| 235 | -5.392721558 | 4.937084961 | 6.753948975 | 1583005690333 | 2.344 | 270 | -5.229727173 | 4.942916870 | 6.768753052 | 1583005690684 | 2.695 |
| 236 | -5.379412842 | 4.929757690 | 6.779519653 | 1583005690343 | 2.354 | 271 | -5.173352051 | 4.941870117 | 6.801052856 | 1583005690694 | 2.705 |
| 237 | -5.380310059 | 4.946954346 | 6.830810547 | 1583005690353 | 2.364 | 272 | -5.134024048 | 4.930355835 | 6.794174194 | 1583005690705 | 2.716 |
| 238 | -5.335748291 | 4.909570313 | 6.821389771 | 1583005690364 | 2.375 | 273 | -5.128042603 | 4.905084229 | 6.796566772 | 1583005690714 | 2.725 |
| 239 | -5.270999146 | 4.916897583 | 6.739473042 | 1583005690374 | 2.385 | 274 | -5.141949463 | 4.844372559 | 6.749612427 | 1583005690725 | 2.736 |
| 240 | -5.210586548 | 4.951739502 | 6.645535278 | 1583005690384 | 2.395 | 275 | -5.165725708 | 4.835848999 | 6.657049561 | 1583005690735 | 2.746 |
| 241 | -5.149575806 | 4.960562134 | 6.604412842 | 1583005690393 | 2.404 | 276 | -5.179632568 | 4.881457520 | 6.437380981 | 1583005690745 | 2.756 |
| 242 | -5.104864502 | 4.976113892 | 6.653012085 | 1583005690404 | 2.415 | 277 | -5.222399902 | 4.928411865 | 6.438577271 | 1583005690754 | 2.765 |
| 243 | -5.110098267 | 4.996002197 | 6.804940796 | 1583005690414 | 2.425 | 278 | -5.313766479 | 5.026058960 | 6.548785400 | 1583005690765 | 2.776 |
| 244 | -5.136865234 | 4.995553589 | 6.884793091 | 1583005690424 | 2.435 | 279 | -5.349954224 | 5.118771362 | 6.611740112 | 1583005690774 | 2.785 |
| 245 | -5.207147217 | 5.040563965 | 6.876718140 | 1583005690434 | 2.445 | 280 | -5.247073364 | 5.042507935 | 6.746472168 | 1583005690784 | 2.795 |

FIG. 6D

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 281 | -5.224792480 | 4.952337646 | 6.862362671 | 1583005690794 | 2.805 | 316 | -5.314813232 | 4.905383301 | 6.608300781 | 1583005691145 | 3.156 |
| 282 | -5.258737183 | 4.920486450 | 6.916644287 | 1583005690804 | 2.815 | 317 | -5.440124512 | 5.006918335 | 6.796716309 | 1583005691155 | 3.166 |
| 283 | -5.279373169 | 4.870989990 | 6.959112549 | 1583005690815 | 2.826 | 318 | -5.413656616 | 4.973123169 | 6.846212769 | 1583005691165 | 3.176 |
| 284 | -5.283111572 | 4.809530640 | 7.010403442 | 1583005690825 | 2.836 | 319 | -5.315560913 | 4.903289795 | 6.980047607 | 1583005691175 | 3.186 |
| 285 | -5.225540161 | 4.790240479 | 7.114929199 | 1583005690835 | 2.846 | 320 | -5.217614746 | 4.793530273 | 7.001730347 | 1583005691185 | 3.196 |
| 286 | -5.118472290 | 4.803100586 | 7.168762207 | 1583005690847 | 2.858 | 321 | -5.279522705 | 4.766912842 | 6.979598999 | 1583005691195 | 3.206 |
| 287 | -5.224493408 | 4.825680542 | 6.912008667 | 1583005690857 | 2.868 | 322 | -5.402890015 | 4.783212280 | 6.992160034 | 1583005691206 | 3.217 |
| 288 | -5.399749756 | 4.740145874 | 6.839035034 | 1583005690865 | 2.876 | 323 | -5.475564575 | 4.780221558 | 7.001730347 | 1583005691216 | 3.227 |
| 289 | -5.605661011 | 4.630535889 | 6.782360840 | 1583005690876 | 2.887 | 324 | -5.564987183 | 4.841232300 | 6.988421631 | 1583005691226 | 3.237 |
| 290 | -5.717514038 | 4.655508423 | 6.565234375 | 1583005690887 | 2.898 | 325 | -5.645288086 | 4.897756958 | 6.923074341 | 1583005691236 | 3.247 |
| 291 | -5.729327393 | 4.833605957 | 6.244927979 | 1583005690894 | 2.905 | 326 | -5.633773804 | 4.920935059 | 6.810623169 | 1583005691246 | 3.257 |
| 292 | -5.807684326 | 5.071368408 | 6.008511353 | 1583005690905 | 2.916 | 327 | -5.560501099 | 4.913458252 | 6.692340088 | 1583005691256 | 3.267 |
| 293 | -5.883648682 | 5.229727173 | 6.028100586 | 1583005690914 | 2.925 | 328 | -5.461807251 | 4.890878296 | 6.637759399 | 1583005691266 | 3.277 |
| 294 | -5.844619751 | 5.168417358 | 6.162832642 | 1583005690924 | 2.935 | 329 | -5.413357544 | 4.904336548 | 6.609945679 | 1583005691276 | 3.287 |
| 295 | -5.765066528 | 5.044900513 | 6.391024780 | 1583005690934 | 2.945 | 330 | -5.364608765 | 4.951290894 | 6.619815063 | 1583005691286 | 3.297 |
| 296 | -5.567080688 | 4.906729126 | 6.517382813 | 1583005690945 | 2.956 | 331 | -5.268756104 | 5.001086426 | 6.715368652 | 1583005691296 | 3.307 |
| 297 | -5.396459961 | 4.818502808 | 6.447549438 | 1583005690955 | 2.966 | 332 | -5.179632568 | 4.990170288 | 6.779220581 | 1583005691306 | 3.317 |
| 298 | -5.388085938 | 4.824633789 | 6.416894531 | 1583005690965 | 2.976 | 333 | -5.143594360 | 4.880560303 | 6.804641724 | 1583005691316 | 3.327 |
| 299 | -5.386740112 | 4.894616699 | 6.470877075 | 1583005690975 | 2.986 | 334 | -5.176342773 | 4.752258301 | 6.845465088 | 1583005691326 | 3.337 |
| 300 | -5.298812866 | 4.900000000 | 6.511849976 | 1583005690985 | 2.996 | 335 | -5.274887085 | 4.696929932 | 6.768453979 | 1583005691336 | 3.347 |
| 301 | -5.219409180 | 4.897009277 | 6.575402832 | 1583005690995 | 3.006 | 336 | -5.397656250 | 4.741940308 | 6.652114868 | 1583005691346 | 3.357 |
| 302 | -5.229876709 | 4.962954712 | 6.664077759 | 1583005691005 | 3.016 | 337 | -5.461807251 | 4.848858643 | 6.517980957 | 1583005691356 | 3.367 |
| 303 | -5.260681152 | 4.981945801 | 6.623403931 | 1583005691015 | 3.026 | 338 | -5.469284058 | 4.966992188 | 6.454129028 | 1583005691367 | 3.378 |
| 304 | -5.254849243 | 4.940972900 | 6.531887817 | 1583005691025 | 3.036 | 339 | -5.421282959 | 5.004974365 | 6.474914551 | 1583005691377 | 3.388 |
| 305 | -5.236904907 | 4.908822632 | 6.477606201 | 1583005691036 | 3.047 | 340 | -5.379263306 | 5.007366943 | 6.593496704 | 1583005691387 | 3.398 |
| 306 | -5.301055908 | 4.961907959 | 6.497943115 | 1583005691045 | 3.056 | 341 | -5.339935303 | 5.008712769 | 6.699368286 | 1583005691396 | 3.407 |
| 307 | -5.345916748 | 5.007815552 | 6.583029175 | 1583005691056 | 3.067 | 342 | -5.319299316 | 4.969683838 | 6.733761597 | 1583005691407 | 3.418 |
| 308 | -5.327075195 | 4.958020020 | 6.582879639 | 1583005691065 | 3.076 | 343 | -5.336346436 | 4.941571045 | 6.749761963 | 1583005691417 | 3.428 |
| 309 | -5.341580200 | 4.867251587 | 6.590655518 | 1583005691075 | 3.086 | 344 | -5.409170532 | 4.959664917 | 6.735556030 | 1583005691427 | 3.438 |
| 310 | -5.339785767 | 4.805194092 | 6.593646240 | 1583005691101 | 3.112 | 345 | -5.440124512 | 5.011404419 | 6.617272949 | 1583005691437 | 3.448 |
| 311 | -5.346813965 | 4.763323975 | 6.552253804 | 1583005691102 | 3.113 | 346 | -5.430404663 | 5.063592529 | 6.476409912 | 1583005691447 | 3.458 |
| 312 | -5.361169434 | 4.774838257 | 6.514840698 | 1583005691105 | 3.116 | 347 | -5.397955322 | 5.132379150 | 6.435586548 | 1583005691457 | 3.468 |
| 313 | -5.360870361 | 4.814016724 | 6.501831055 | 1583005691116 | 3.127 | 348 | -5.305093384 | 5.139407349 | 6.434390259 | 1583005691467 | 3.478 |
| 314 | -5.283261108 | 4.853942871 | 6.490316772 | 1583005691125 | 3.136 | 349 | -5.215521240 | 5.093649292 | 6.492410278 | 1583005691476 | 3.487 |
| 315 | -5.225988770 | 4.867102051 | 6.481494141 | 1583005691135 | 3.146 | 350 | -5.172604370 | 5.124304199 | 6.487475586 | 1583005691487 | 3.498 |

FIG. 6E

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 351 | -5.204306030 | 5.205502319 | 6.419985254 | 1583005691497 | 3.508 | 386 | -5.280868530 | 5.367449951 | 6.270648193 | 1583005691848 | 3.859 |
| 352 | -5.209390259 | 5.227334595 | 6.446353149 | 1583005691507 | 3.518 | 387 | -5.239746094 | 5.373431396 | 6.168814087 | 1583005691858 | 3.869 |
| 353 | -5.209838867 | 5.221054077 | 6.437829590 | 1583005691517 | 3.528 | 388 | -5.218362427 | 5.395562744 | 6.069522095 | 1583005691868 | 3.879 |
| 354 | -5.233166504 | 5.241839600 | 6.435736084 | 1583005691527 | 3.538 | 389 | -5.202062988 | 5.406628418 | 6.033633423 | 1583005691878 | 3.889 |
| 355 | -5.228530884 | 5.291336060 | 6.411660767 | 1583005691537 | 3.548 | 390 | -5.185464478 | 5.415750122 | 6.078494263 | 1583005691888 | 3.899 |
| 356 | -5.219558716 | 5.275335693 | 6.377117920 | 1583005691547 | 3.558 | 391 | -5.139706421 | 5.375674438 | 6.104962158 | 1583005691898 | 3.909 |
| 357 | -5.261279297 | 5.288195801 | 6.388482666 | 1583005691557 | 3.568 | 392 | -5.008563232 | 5.305691528 | 6.152514648 | 1583005691908 | 3.919 |
| 358 | -5.264868164 | 5.306289673 | 6.318200684 | 1583005691567 | 3.578 | 393 | -4.886093140 | 5.258438110 | 6.230123901 | 1583005691918 | 3.929 |
| 359 | -5.302252197 | 5.383001709 | 6.179431152 | 1583005691577 | 3.588 | 394 | -4.842279053 | 5.244680786 | 6.332406616 | 1583005691928 | 3.939 |
| 360 | -5.335897827 | 5.448498535 | 6.193487549 | 1583005691587 | 3.598 | 395 | -4.915850830 | 5.253652954 | 6.467886353 | 1583005691938 | 3.949 |
| 361 | -5.295971680 | 5.373431396 | 6.253302002 | 1583005691597 | 3.608 | 396 | -5.015441895 | 5.217465210 | 6.624899292 | 1583005691948 | 3.959 |
| 362 | -5.322439575 | 5.384796143 | 6.350500488 | 1583005691607 | 3.618 | 397 | -5.170211792 | 5.223446655 | 6.709088135 | 1583005691958 | 3.969 |
| 363 | -5.341131592 | 5.377020264 | 6.392819214 | 1583005691617 | 3.628 | 398 | -5.343823242 | 5.266363525 | 6.741537476 | 1583005691968 | 3.979 |
| 364 | -5.344720459 | 5.333355713 | 6.418838501 | 1583005691627 | 3.638 | 399 | -5.454479980 | 5.285653687 | 6.795669556 | 1583005691978 | 3.989 |
| 365 | -5.368347168 | 5.320046997 | 6.438876343 | 1583005691638 | 3.649 | 400 | -5.482592773 | 5.288046265 | 6.870288086 | 1583005691989 | 4.000 |
| 366 | -5.391525269 | 5.322888184 | 6.416894531 | 1583005691647 | 3.658 | 401 | -5.351300049 | 5.253503418 | 6.904083252 | 1583005691998 | 4.009 |
| 367 | -5.404983521 | 5.306140137 | 6.342724609 | 1583005691658 | 3.669 | 402 | -5.190548706 | 5.213128662 | 6.839932251 | 1583005692009 | 4.020 |
| 368 | -5.434591675 | 5.272494507 | 6.306835938 | 1583005691667 | 3.678 | 403 | -5.172006226 | 5.207147217 | 6.857128906 | 1583005692018 | 4.029 |
| 369 | -5.471826172 | 5.281915283 | 6.296817017 | 1583005691678 | 3.689 | 404 | -5.286700439 | 5.194735718 | 6.973019409 | 1583005692029 | 4.040 |
| 370 | -5.463900757 | 5.288943481 | 6.216815186 | 1583005691687 | 3.698 | 405 | -5.316906738 | 5.147332764 | 6.972421265 | 1583005692038 | 4.049 |
| 371 | -5.432498169 | 5.265765381 | 6.185861206 | 1583005691698 | 3.709 | 406 | -5.305841064 | 5.140304565 | 6.773388672 | 1583005692049 | 4.060 |
| 372 | -5.400347900 | 5.300457764 | 6.226983643 | 1583005691707 | 3.718 | 407 | -5.296270752 | 5.183969116 | 6.557757568 | 1583005692058 | 4.069 |
| 373 | -5.352047729 | 5.330664063 | 6.245227051 | 1583005691718 | 3.729 | 408 | -5.308084106 | 5.188903809 | 6.260330200 | 1583005692068 | 4.079 |
| 374 | -5.303598022 | 5.310177612 | 6.343771362 | 1583005691727 | 3.738 | 409 | -5.471527100 | 5.211483765 | 5.549435425 | 1583005692079 | 4.090 |
| 375 | -5.297018433 | 5.312121582 | 6.406277466 | 1583005691737 | 3.748 | 410 | -5.667419434 | 5.279074097 | 6.105859375 | 1583005692088 | 4.099 |
| 376 | -5.315560913 | 5.285803223 | 6.422128296 | 1583005691748 | 3.759 | 411 | -5.834002686 | 5.374478149 | 6.179281616 | 1583005692098 | 4.109 |
| 377 | -5.334402466 | 5.249465942 | 6.394763184 | 1583005691758 | 3.769 | 412 | -5.673550415 | 5.191595459 | 6.234609985 | 1583005692108 | 4.119 |
| 378 | -5.339337158 | 5.245428467 | 6.350051880 | 1583005691768 | 3.779 | 413 | -5.556314087 | 4.844223022 | 6.511700439 | 1583005692119 | 4.130 |
| 379 | -5.341131592 | 5.260382080 | 6.305639648 | 1583005691778 | 3.789 | 414 | -5.653512573 | 4.695584106 | 6.549981689 | 1583005692129 | 4.140 |
| 380 | -5.373580933 | 5.312271118 | 6.308032227 | 1583005691788 | 3.799 | 415 | -5.812319946 | 4.642947388 | 6.561346436 | 1583005692139 | 4.150 |
| 381 | -5.385693359 | 5.364608765 | 6.338986206 | 1583005691798 | 3.809 | 416 | -5.969631958 | 4.515243530 | 6.647778320 | 1583005692149 | 4.160 |
| 382 | -5.407525635 | 5.384945679 | 6.404034424 | 1583005691808 | 3.819 | 417 | -6.098681641 | 4.442568970 | 6.593945313 | 1583005692158 | 4.169 |
| 383 | -5.423226929 | 5.382553101 | 6.446353149 | 1583005691818 | 3.829 | 418 | -6.341976929 | 4.562646484 | 6.386837769 | 1583005692168 | 4.179 |
| 384 | -5.386889648 | 5.376123047 | 6.412408447 | 1583005691828 | 3.839 | 419 | -6.405828857 | 4.845419312 | 6.040213013 | 1583005692179 | 4.190 |
| 385 | -5.333804321 | 5.364010620 | 6.354837036 | 1583005691838 | 3.849 | 420 | -6.242086792 | 5.089013672 | 5.695382690 | 1583005692188 | 4.199 |

FIG. 6F

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 421 | -6.053521729 | 5.165725708 | 5.572164917 | 1583005692198 | 4.209 | 456 | -5.676242065 | 5.118621826 | 6.477157593 | 1583005692550 | 4.561 |
| 422 | -5.926266479 | 5.145388794 | 5.652316284 | 1583005692208 | 4.219 | 457 | -5.684765625 | 5.128491211 | 6.377267456 | 1583005692560 | 4.571 |
| 423 | -5.846713257 | 5.156903076 | 5.822787476 | 1583005692218 | 4.229 | 458 | -5.661288452 | 5.105014038 | 6.282760620 | 1583005692570 | 4.581 |
| 424 | -5.744729614 | 5.151818848 | 5.970678711 | 1583005692228 | 4.239 | 459 | -5.627792358 | 5.074807739 | 6.225189209 | 1583005692580 | 4.591 |
| 425 | -5.639904785 | 5.071517944 | 6.069223022 | 1583005692238 | 4.249 | 460 | -5.603268433 | 5.045797729 | 6.229376221 | 1583005692590 | 4.601 |
| 426 | -5.627343750 | 5.080938721 | 6.125598145 | 1583005692248 | 4.259 | 461 | -5.549884033 | 5.024713135 | 6.273638916 | 1583005692600 | 4.611 |
| 427 | -5.666223145 | 5.097238159 | 6.157449341 | 1583005692259 | 4.270 | 462 | -5.482891846 | 5.000488281 | 6.272891235 | 1583005692610 | 4.621 |
| 428 | -5.677288818 | 5.087667847 | 6.197076416 | 1583005692268 | 4.279 | 463 | -5.441918945 | 5.003179932 | 6.263619995 | 1583005692620 | 4.631 |
| 429 | -5.658596802 | 5.023367310 | 6.225787354 | 1583005692278 | 4.289 | 464 | -5.431152344 | 5.024264526 | 6.211282349 | 1583005692630 | 4.641 |
| 430 | -5.636764526 | 4.984936523 | 6.233413696 | 1583005692289 | 4.300 | 465 | -5.429806519 | 5.070172119 | 6.190048218 | 1583005692640 | 4.651 |
| 431 | -5.647979736 | 5.005273438 | 6.238647461 | 1583005692299 | 4.310 | 466 | -5.428610229 | 5.095742798 | 6.229226685 | 1583005692650 | 4.661 |
| 432 | -5.653063965 | 5.097088623 | 6.161038208 | 1583005692309 | 4.320 | 467 | -5.424124146 | 5.108004761 | 6.294723511 | 1583005692660 | 4.671 |
| 433 | -5.593847656 | 5.142398071 | 6.048287964 | 1583005692319 | 4.330 | 468 | -5.445059204 | 5.098284912 | 6.322088623 | 1583005692670 | 4.681 |
| 434 | -5.504873657 | 5.125500488 | 6.000735474 | 1583005692329 | 4.340 | 469 | -5.551977539 | 5.048190308 | 6.367398071 | 1583005692680 | 4.691 |
| 435 | -5.458218384 | 5.083480835 | 6.033633423 | 1583005692339 | 4.350 | 470 | -5.653512573 | 4.985833740 | 6.388034058 | 1583005692690 | 4.701 |
| 436 | -5.494555664 | 5.064489746 | 6.064587402 | 1583005692349 | 4.360 | 471 | -5.733514404 | 4.976412964 | 6.303396606 | 1583005692701 | 4.712 |
| 437 | -5.573211670 | 5.106658936 | 6.061746216 | 1583005692359 | 4.370 | 472 | -5.770748901 | 5.028900146 | 6.201412964 | 1583005692710 | 4.721 |
| 438 | -5.615081787 | 5.174996948 | 6.062493896 | 1583005692369 | 4.380 | 473 | -5.743682861 | 5.066882324 | 6.139953613 | 1583005692721 | 4.732 |
| 439 | -5.554071045 | 5.249017334 | 6.007763672 | 1583005692379 | 4.390 | 474 | -5.687756348 | 5.085723877 | 6.167767334 | 1583005692731 | 4.742 |
| 440 | -5.518780518 | 5.193988037 | 5.971875000 | 1583005692389 | 4.400 | 475 | -5.652316284 | 5.075405884 | 6.276031494 | 1583005692741 | 4.752 |
| 441 | -5.541360474 | 5.067779541 | 6.122906494 | 1583005692399 | 4.410 | 476 | -5.630932617 | 5.062994385 | 6.397006226 | 1583005692751 | 4.762 |
| 442 | -5.532986450 | 4.978955078 | 6.208889771 | 1583005692410 | 4.421 | 477 | -5.557659912 | 5.025161743 | 6.457867432 | 1583005692761 | 4.772 |
| 443 | -5.556613159 | 4.962207031 | 6.233563232 | 1583005692420 | 4.431 | 478 | -5.522967529 | 4.976113892 | 6.483288574 | 1583005692771 | 4.782 |
| 444 | -5.590258789 | 4.978656006 | 6.220254517 | 1583005692429 | 4.440 | 479 | -5.550631714 | 4.998245239 | 6.470278931 | 1583005692781 | 4.792 |
| 445 | -5.595043945 | 4.992562866 | 6.217861938 | 1583005692440 | 4.451 | 480 | -5.556613159 | 5.064639282 | 6.384893799 | 1583005692791 | 4.802 |
| 446 | -5.570220947 | 4.996151733 | 6.215469360 | 1583005692450 | 4.461 | 481 | -5.519677734 | 5.102172852 | 6.362014771 | 1583005692806 | 4.817 |
| 447 | -5.625549316 | 5.030545044 | 6.305639648 | 1583005692460 | 4.471 | 482 | -5.451040649 | 5.133874512 | 6.401641846 | 1583005692810 | 4.821 |
| 448 | -5.705999756 | 5.099182129 | 6.555514526 | 1583005692470 | 4.481 | 483 | -5.412759399 | 5.134771729 | 6.400296021 | 1583005692820 | 4.831 |
| 449 | -5.598333740 | 5.057760620 | 6.705648804 | 1583005692480 | 4.491 | 484 | -5.448947144 | 5.100976563 | 6.451138306 | 1583005692830 | 4.841 |
| 450 | -5.544500732 | 5.034133911 | 6.837689209 | 1583005692490 | 4.501 | 485 | -5.490368652 | 5.080041504 | 6.469232178 | 1583005692840 | 4.851 |
| 451 | -5.525360107 | 5.022769165 | 6.848754883 | 1583005692500 | 4.511 | 486 | -5.533734131 | 5.076751709 | 6.414352417 | 1583005692851 | 4.862 |
| 452 | -5.494406128 | 5.016339111 | 6.784155273 | 1583005692510 | 4.521 | 487 | -5.547640991 | 5.106210327 | 6.344967651 | 1583005692860 | 4.871 |
| 453 | -5.514294434 | 5.030545044 | 6.706695557 | 1583005692520 | 4.531 | 488 | -5.514743042 | 5.157501221 | 6.292630005 | 1583005692871 | 4.882 |
| 454 | -5.587716675 | 5.074359131 | 6.654058838 | 1583005692530 | 4.541 | 489 | -5.487377930 | 5.173052979 | 6.333453369 | 1583005692880 | 4.891 |
| 455 | -5.643792725 | 5.105761719 | 6.571215820 | 1583005692540 | 4.551 | 490 | -5.448947144 | 5.149575806 | 6.389080811 | 1583005692891 | 4.902 |

FIG. 6G

| MOTION DATA POINT # | x | y | z | TIME STAMP | TIME ELAPSED | MOTION DATA POINT # | x | y | z | TIME STAMP | TIME ELAPSED |
|---|---|---|---|---|---|---|---|---|---|---|---|
| 491 | -5.434591675 | 5.129388428 | 6.465194702 | 1583005692900 | 4.911 | 526 | -5.457321167 | 5.122808838 | 6.858325195 | 1583005693251 | 5.262 |
| 492 | -5.416198730 | 5.089611816 | 6.499438477 | 1583005692911 | 4.922 | 527 | -5.415750122 | 4.951440430 | 6.981692505 | 1583005693262 | 5.273 |
| 493 | -5.467938232 | 5.092153931 | 6.462353516 | 1583005692921 | 4.932 | 528 | -5.346963501 | 4.734463501 | 7.061096191 | 1583005693271 | 5.282 |
| 494 | -5.509957886 | 5.114584351 | 6.404333496 | 1583005692931 | 4.942 | 529 | -5.249465942 | 4.511505127 | 6.958065796 | 1583005693282 | 5.293 |
| 495 | -5.543304443 | 5.109948730 | 6.316406250 | 1583005692941 | 4.952 | 530 | -5.252905273 | 4.475466919 | 6.698022461 | 1583005693292 | 5.303 |
| 496 | -5.572015381 | 5.119967651 | 6.269601440 | 1583005692951 | 4.962 | 531 | -5.327822876 | 4.565786743 | 6.389230347 | 1583005693302 | 5.313 |
| 497 | -5.606109619 | 5.138809204 | 6.239395142 | 1583005692961 | 4.972 | 532 | -5.437582397 | 4.676892090 | 6.166870117 | 1583005693312 | 5.323 |
| 498 | -5.623754883 | 5.167819214 | 6.215319824 | 1583005692971 | 4.982 | 533 | -5.519378662 | 4.763922119 | 6.182421875 | 1583005693322 | 5.333 |
| 499 | -5.597735596 | 5.128192139 | 6.184216309 | 1583005692981 | 4.992 | 534 | -5.572314453 | 4.850054932 | 6.338986206 | 1583005693332 | 5.343 |
| 500 | -5.592651367 | 5.073013306 | 6.187207031 | 1583005692991 | 5.002 | 535 | -5.612689209 | 4.882803345 | 6.515887451 | 1583005693342 | 5.353 |
| 501 | -5.592501831 | 5.090957642 | 6.185113525 | 1583005693001 | 5.012 | 536 | -5.599230957 | 4.830764771 | 6.616525269 | 1583005693352 | 5.363 |
| 502 | -5.591006470 | 5.104565430 | 6.152365112 | 1583005693012 | 5.023 | 537 | -5.642895508 | 4.790988159 | 6.635217285 | 1583005693362 | 5.373 |
| 503 | -5.570220947 | 5.077648926 | 6.149224854 | 1583005693021 | 5.032 | 538 | -5.732019043 | 4.793530273 | 6.590655518 | 1583005693372 | 5.383 |
| 504 | -5.566033936 | 5.057760620 | 6.188552856 | 1583005693032 | 5.043 | 539 | -5.841180420 | 4.815811157 | 6.553869629 | 1583005693382 | 5.393 |
| 505 | -5.561248779 | 5.072116089 | 6.243881226 | 1583005693041 | 5.052 | 540 | -5.885891724 | 4.771548462 | 6.562094116 | 1583005693392 | 5.403 |
| 506 | -5.562295532 | 5.101425171 | 6.243731689 | 1583005693052 | 5.063 | 541 | -5.849918823 | 4.722052002 | 6.582580566 | 1583005693402 | 5.413 |
| 507 | -5.563641357 | 5.122061157 | 6.212179565 | 1583005693061 | 5.072 | 542 | -5.777328491 | 4.679882813 | 6.571963501 | 1583005693412 | 5.423 |
| 508 | -5.583380127 | 5.169015503 | 6.218011475 | 1583005693072 | 5.083 | 543 | -5.739495850 | 4.720407104 | 6.574356079 | 1583005693422 | 5.433 |
| 509 | -5.590557861 | 5.167968750 | 6.190048218 | 1583005693081 | 5.092 | 544 | -5.648727417 | 4.753155518 | 6.614880371 | 1583005693432 | 5.443 |
| 510 | -5.592950439 | 5.144641113 | 6.235058594 | 1583005693092 | 5.103 | 545 | -5.506069946 | 4.751510620 | 6.634020996 | 1583005693443 | 5.454 |
| 511 | -5.581286621 | 5.109799194 | 6.249862671 | 1583005693101 | 5.112 | 546 | -5.468087769 | 4.763323975 | 6.667517090 | 1583005693452 | 5.463 |
| 512 | -5.576950073 | 5.107556152 | 6.236254883 | 1583005693112 | 5.123 | 547 | -5.512200928 | 4.768857739 | 6.711032104 | 1583005693462 | 5.473 |
| 513 | -5.609399414 | 5.119668579 | 6.283358765 | 1583005693122 | 5.133 | 548 | -5.583679199 | 4.767062378 | 6.713723755 | 1583005693473 | 5.484 |
| 514 | -5.713177490 | 5.134622192 | 6.352593994 | 1583005693132 | 5.143 | 549 | -5.660241699 | 4.795922852 | 6.642245483 | 1583005693483 | 5.494 |
| 515 | -5.748916626 | 5.132977295 | 6.417791748 | 1583005693142 | 5.153 | 550 | -5.697177124 | 4.873382568 | 6.590655518 | 1583005693493 | 5.504 |
| 516 | -5.536425781 | 5.050283813 | 6.263021851 | 1583005693152 | 5.163 | 551 | -5.622259521 | 4.909420776 | 6.575253296 | 1583005693503 | 5.514 |
| 517 | -5.467639160 | 5.092153931 | 5.996697998 | 1583005693162 | 5.173 | 552 | -5.502780151 | 4.939328003 | 6.544598389 | 1583005693513 | 5.524 |
| 518 | -5.670111084 | 5.332608032 | 5.968435669 | 1583005693171 | 5.182 | 553 | -5.413058472 | 4.978207397 | 6.545794678 | 1583005693523 | 5.534 |
| 519 | -5.343524170 | 5.309579468 | 6.196029663 | 1583005693181 | 5.192 | 554 | -5.361917114 | 5.040863037 | 6.639254761 | 1583005693533 | 5.544 |
| 520 | -4.767510986 | 5.212380981 | 6.149523926 | 1583005693191 | 5.202 | 555 | -5.317355347 | 5.077349854 | 6.685012817 | 1583005693543 | 5.554 |
| 521 | -4.849157715 | 5.220904541 | 6.346163940 | 1583005693202 | 5.213 | 556 | -5.315261841 | 5.048638916 | 6.697723389 | 1583005693553 | 5.564 |
| 522 | -5.229129028 | 5.148080444 | 6.774136353 | 1583005693211 | 5.222 | 557 | -5.339636230 | 5.014843750 | 6.666320801 | 1583005693563 | 5.574 |
| 523 | -5.391076660 | 5.037722778 | 6.843222046 | 1583005693221 | 5.232 | 558 | -5.361618042 | 5.029199219 | 6.556112671 | 1583005693573 | 5.584 |
| 524 | -5.447302246 | 5.060900879 | 6.715069580 | 1583005693232 | 5.242 | 559 | -5.380310059 | 5.067480469 | 6.444857788 | 1583005693583 | 5.594 |
| 525 | -5.475115967 | 5.162136841 | 6.702359009 | 1583005693241 | 5.252 | 560 | -5.367599487 | 5.111743164 | 6.408969116 | 1583005693593 | 5.604 |

FIG. 6H

| MOTION DATA POINT # | x | y | z | TIME STAMP | TIME ELAPSED |
|---|---|---|---|---|---|
| 561 | -5.325280762 | 5.088415527 | 6.407623291 | 1583005693603 | 5.614 |
| 562 | -5.322439575 | 5.004077148 | 6.509906006 | 1583005693613 | 5.624 |
| 563 | -5.346963501 | 4.999142456 | 6.591702271 | 1583005693623 | 5.634 |
| 564 | -5.372384644 | 5.045050049 | 6.539514160 | 1583005693634 | 5.645 |
| 565 | -5.394067383 | 5.072863770 | 6.515139771 | 1583005693643 | 5.654 |
| 566 | -5.417694092 | 5.027105713 | 6.472222900 | 1583005693653 | 5.664 |
| 567 | -5.467190552 | 4.998544312 | 6.488522339 | 1583005693663 | 5.674 |
| 568 | -5.486032104 | 5.024862671 | 6.423025513 | 1583005693673 | 5.684 |
| 569 | -5.522219849 | 5.028302002 | 6.320443726 | 1583005693683 | 5.694 |
| 570 | -5.562445068 | 4.967590332 | 6.278125000 | 1583005693693 | 5.704 |
| 571 | -5.572015381 | 4.923028564 | 6.212329102 | 1583005693703 | 5.714 |
| 572 | -5.609548950 | 4.950393677 | 6.105111694 | 1583005693713 | 5.724 |
| 573 | -5.628390503 | 4.997348022 | 6.029745483 | 1583005693723 | 5.734 |
| 574 | -5.701214600 | 5.077349854 | 6.069821167 | 1583005693733 | 5.744 |
| 575 | -5.787945557 | 5.062545776 | 6.113784790 | 1583005693743 | 5.754 |
| 576 | -5.691943359 | 5.023367310 | 6.169412231 | 1583005693753 | 5.764 |
| 577 | -5.514144897 | 4.997796631 | 6.215020752 | 1583005693763 | 5.774 |
| 578 | -5.394964600 | 5.019778442 | 5.906378174 | 1583005693775 | 5.786 |
| 579 | -5.626296997 | 5.262176514 | 5.866152954 | 1583005693783 | 5.794 |
| 580 | -5.590258789 | 5.368048096 | 6.044998169 | 1583005693794 | 5.805 |
| 581 | -4.945608521 | 5.082135010 | 6.182421875 | 1583005693805 | 5.816 |
| 582 | -4.843774414 | 4.969235229 | 6.158645630 | 1583005693813 | 5.824 |
| 583 | -5.258737183 | 4.951141357 | 6.612338257 | 1583005693825 | 5.836 |
| 584 | -5.623455811 | 4.948898315 | 6.779220581 | 1583005693833 | 5.844 |
| 585 | -5.708392334 | 5.003329468 | 6.670059204 | 1583005693844 | 5.855 |

FIG. 6I

| TOUCH FEATURE | SAMPLE #1 | SAMPLE #2 | SAMPLE #3 | SAMPLE #4 | SAMPLE #5 | MEAN | STD DEV. |
|---|---|---|---|---|---|---|---|
| distance_covered | 200.3943288 | 144.4882413 | 108.7467056 | 112.1910469 | 123.0347651 | 196.713947 | 48.93410519 |
| distance_spanned | 195.0025641 | 140.8801628 | 105.0259226 | 111.8754369 | 122.639938 | 192.8024784 | 48.00711398 |
| efficiency | 0.973094225 | 0.975028567 | 0.965784867 | 0.997186852 | 0.996790931 | 0.979770994 | 0.04002827 |
| duration | 0.177000046 | 0.156000137 | 0.088000059 | 0.078000069 | 0.080000162 | 0.159024022 | 0.22048788 |
| speed | 1132.171056 | 926.2058597 | 1235.757187 | 1438.345489 | 1537.931447 | 1496.2145 | 423.03928221 |
| num_points | 14 | 8 | 8 | 8 | 8 | 11.11572052 | 4.97743090 |
| curvature | 5.112918204 | 9.081795576 | 7.388606154 | 13.08333366 | 14.34289181 | 8.508351958 | 4.35105405 |
| pressure_median | 0.316666667 | 0.250000000 | 0.441666667 | 0.233333333 | 0.366666667 | 0.46084425 | 0.21843640 |
| pressure_mean | 0.326190476 | 0.214583333 | 0.429166667 | 0.202083333 | 0.335416667 | 0.413835073 | 0.19910231 |
| pressure_std | 0.149888033 | 0.087485827 | 0.054736019 | 0.084720596 | 0.063269078 | 0.184264809 | 0.11866428 |
| pressure_max | 0.483333333 | 0.250000000 | 0.483333333 | 0.250000000 | 0.366666667 | 0.583442504 | 0.32487166 |
| pressure_min | 0.000000000 | 0.000000000 | 0.366666667 | 0.000000000 | 0.183333333 | 0.05356623 | 0.10549849 |
| radiusMin_median | 6.058776855 | 6.058776855 | 6.058776855 | 6.058776855 | 10.097961430 | 8.510508975 | 2.03940565 |
| radiusMin_mean | 6.635803223 | 4.039184570 | 5.553878784 | 4.039184570 | 7.068572998 | 6.609300421 | 1.48880792 |
| radiusMin_std | 4.148667403 | 3.739558262 | 5.034534387 | 3.739558262 | 5.609337393 | 4.609660965 | 0.86525078 |
| radiusMin_max | 10.097961430 | 6.058776855 | 10.097961430 | 6.058776855 | 10.097961430 | 9.61290651 | 2.08806083 |
| radiusMin_min | -2.019592285 | -2.019592285 | -2.019592285 | -2.019592285 | -2.019592285 | -2.019592285 | 1.00000000 |
| radiusMax_median | 10.09796143 | 10.09796143 | 10.09796143 | 10.09796143 | 14.13714600 | 12.549969354 | 2.03940565 |
| radiusMax_mean | 10.674987790 | 8.078369141 | 9.593063354 | 8.078369141 | 11.107757570 | 10.64848499 | 1.48880792 |
| radiusMax_std | 4.148667403 | 3.739558262 | 5.034534387 | 3.739558262 | 5.609337393 | 4.609660965 | 0.86525078 |
| radiusMax_max | 14.13714600 | 10.09796143 | 14.13714600 | 10.09796143 | 14.13714600 | 13.65209108 | 2.08806083 |
| radiusMax_min | 2.019592285 | 2.019592285 | 2.019592285 | 2.019592285 | 2.019592285 | 2.019592285 | 1.00000000 |
| orientation_median | -1.570796327 | -1.570796327 | -1.570796327 | -1.570796327 | -1.570796327 | -1.570796327 | 4.4409E-16 |
| orientation_mean | -1.570796327 | -1.570796327 | -1.570796327 | -1.570796327 | -1.570796327 | -1.570796327 | 4.7160E-16 |
| orientation_std | 0 | 0 | 0 | 0 | 0 | 0 | 1.00000000 |
| orientation_max | -1.570796327 | -1.570796327 | -1.570796327 | -1.570796327 | -1.570796327 | -1.570796327 | 4.4409E-16 |
| orientation_min | -1.570796327 | -1.570796327 | -1.570796327 | -1.570796327 | -1.570796327 | -1.570796327 | 4.4409E-16 |
| size_median | 0 | 0 | 0 | 0 | 0 | 0 | 1.00000000 |
| size_mean | 0 | 0 | 0 | 0 | 0 | 0 | 1.00000000 |
| size_std | 0 | 0 | 0 | 0 | 0 | 0 | 1.00000000 |
| size_max | 0 | 0 | 0 | 0 | 0 | 0 | 1.00000000 |
| size_min | 0 | 0 | 0 | 0 | 0 | 0 | 1.00000000 |
| beginning_timestamp | 1583005689576 | 1583005690747 | 1583005692082 | 1583005693159 | 1583005693774 | | |

FIG. 7

$$\text{distance\_covered} = \sqrt{0^2 + 0^2} + \sqrt{26^2 + (-0.67)^2} + \sqrt{13^2 + (-2)^2} + \sqrt{31^2 + (-4.33)^2} +$$

$$\sqrt{35.33^2 + (-1.33)^2} + \sqrt{39^2 + 0^2} + \sqrt{23^2 + 3^2} + \sqrt{12.33^2 + 5.67^2} +$$

$$\sqrt{5^2 + 3.33^2} + \sqrt{3.33^2 + 0.33^2} + \sqrt{3^2 + 0^2} + \sqrt{0.67^2 + (-1.33)^2} +$$

$$\sqrt{3.33^2 + (-3.67)^2} + \sqrt{0^2 + 0^2} = 200.394$$

FIG. 8

$$\text{distance\_covered} = \sqrt{(329.67 - 134.67)^2 + (498.67 - 499.67)^2} = 195.003$$

FIG. 9

| MOTION FEATURE | SAMPLE #1 | MEAN | STD DEV. |
|---|---|---|---|
| mean_x | -0.024240409 | -0.002104825 | 0.058576754 |
| std_x | 0.570215483 | 0.248511626 | 0.244144448 |
| var_x | 0.325145697 | 0.12136454 | 0.249484266 |
| mean_y | 0.050676109 | -0.003703961 | 0.035327411 |
| std_y | 0.343316453 | 0.165261598 | 0.188209960 |
| var_y | 0.117866187 | 0.062734385 | 0.152682585 |
| mean_z | -0.054463822 | 0.000360195 | 0.044614260 |
| std_z | 0.581245425 | 0.258490344 | 0.234225583 |
| var_z | 0.337846244 | 0.121678881 | 0.243848534 |
| mean_overall | -0.009342707 | -0.001816197 | 0.023242719 |
| median_overall | 0.108374185 | -0.000891254 | 0.021530376 |
| std_overall | 0.511583618 | 0.23646247 | 0.217929773 |
| var_overall | 0.261717799 | 0.103407885 | 0.208563728 |
| amax_overall | 1.154840894 | 1.118182243 | 0.919921575 |
| amin_overall | -1.653267492 | -1.108196485 | 0.866980708 |
| mean_l2_norm | 0.790719068 | 0.329969082 | 0.336060555 |
| mean_l1_norm | 1.251425911 | 0.489044881 | 0.507196125 |
| root_mean_sq | 0.886236568 | 0.410953884 | 0.378115233 |
| curve_len | 44.21030212 | 41.60355872 | 48.565209759 |
| diff_entropy | 4.100031679 | 3.648857218 | 0.447326960 |
| energy | 1590.153664 | 1001.205673 | 877.808511671 |
| std_energy | 18.80770331 | 8.354404679 | 7.790953620 |
| peak_magnitude | 240.2611593 | 64.73442254 | 66.206873710 |
| peak_magnitude_frequency | 0.200400802 | 1.729694323 | 3.272812499 |
| peak_power | 2.313644276 | 0.340720568 | 0.712688405 |
| peak_power_frequency | 0.200400802 | 1.828384279 | 3.301842480 |
| magnitude_entropy | 1.329213851 | 1.946328393 | 0.334757071 |
| power_entropy | 0.330635092 | 1.108734983 | 0.398630121 |
| energy_pct_between_3_and_7 | 0.26555102 | 0.280958267 | 0.081761523 |
| beginning_timestamp | 1583005687989 | | |

FIG. 10

| TOUCH AND MOTION FEATURES | NORMALIZED VALUES FOR TOUCH SAMPLE #1 | NORMALIZED VALUES FOR TOUCH SAMPLE #2 | NORMALIZED VALUES FOR TOUCH SAMPLE #3 | LOGISTIC REGRESSION PARAMETER VALUE |
|---|---|---|---|---|
| distance_covered | 0.075210975 | -1.067265979 | -1.797667314 | 0.039499071 |
| distance_spanned | 0.045828327 | -1.081554612 | -1.82840726 | -0.020806062 |
| efficiency | -0.166801320 | -0.118476942 | -0.349406205 | 0.051600519 |
| duration | 0.081528399 | -0.013714514 | -0.322121838 | 0.103562547 |
| speed | -0.860542883 | -1.347413027 | -0.615681151 | 0.037075684 |
| num_points | 0.579471525 | -0.625969619 | -0.625969619 | -0.047807278 |
| curvature | -0.780370391 | 0.131794184 | -0.25735047 | -0.002449288 |
| pressure_median | -0.660043757 | -0.965243192 | -0.087794816 | -0.196025356 |
| pressure_mean | -0.440198788 | -1.000750502 | 0.077003593 | 0.201103401 |
| pressure_std | -0.289697759 | -0.815569622 | -1.091556696 | -0.035286139 |
| pressure_max | -0.308149904 | -1.026382251 | -0.308149904 | -0.023775459 |
| pressure_min | -0.507744049 | -0.507744049 | 2.967819154 | -0.024859793 |
| radiusMin_median | -1.202179725 | -1.202179725 | -1.202179725 | 0.005853785 |
| radiusMin_mean | 0.017801357 | -1.726291096 | -0.708903831 | 0.024220766 |
| radiusMin_std | -0.532786072 | -1.005607540 | 0.491040787 | 0.001510142 |
| radiusMin_max | 0.232299226 | -1.702119786 | 0.232299226 | 0.000267563 |
| radiusMin_min | 0 | 0 | 0 | 0.280999466 |
| radiusMax_median | -1.202179725 | -1.202179725 | -1.202179725 | 0.005853785 |
| radiusMax_mean | 0.017801357 | -1.726291096 | -0.708903831 | 0.024220766 |
| radiusMax_std | -0.532786072 | -1.005607540 | 0.491040787 | 0.001510142 |
| radiusMax_max | 0.232299226 | -1.702119786 | 0.232299226 | 0.000267563 |
| radiusMax_min | 0 | 0 | 0 | -0.143184702 |
| orientation_median | 1 | 1 | 1 | -0.047852157 |
| orientation_mean | 0.470833744 | 0.941667488 | 0.941667488 | 0.010849179 |
| orientation_std | 0 | 0 | 0 | 0 |
| orientation_max | 1 | 1 | 1 | -0.047852157 |
| orientation_min | 1 | 1 | 1 | -0.047852157 |
| size_median | 0 | 0 | 0 | 0.191167797 |
| size_mean | 0 | 0 | 0 | 0.052689479 |
| size_std | 0 | 0 | 0 | -0.216615389 |
| size_max | 0 | 0 | 0 | -0.173557005 |
| size_min | 0 | 0 | 0 | 0.273968542 |
| MOTION FEATURES | | | | |
| mean_x | -0.377890245 | -0.377890245 | -0.377890245 | -0.077619302 |
| std_x | 1.317678363 | 1.317678363 | 1.317678363 | -0.035377923 |
| var_x | 0.816809653 | 0.816809653 | 0.816809653 | -0.029516791 |
| mean_y | 1.539316593 | 1.539316593 | 1.539316593 | -0.016542090 |
| std_y | 0.946043741 | 0.946043741 | 0.946043741 | 0.077078111 |
| var_y | 0.361087690 | 0.361087690 | 0.361087690 | -0.054948878 |
| mean_z | -1.228845133 | -1.228845133 | -1.228845133 | -0.028967649 |
| std_z | 1.377966820 | 1.377966820 | 1.377966820 | -0.407189125 |
| var_z | 0.886482110 | 0.886482110 | 0.886482110 | 0.118696613 |
| mean_overall | -0.323822281 | -0.323822281 | -0.323822281 | 0.017292280 |
| median_overall | 5.074943370 | 5.074943370 | 5.074943370 | 0.000317676 |
| std_overall | 1.262430301 | 1.262430301 | 1.262430301 | 0.700526120 |
| var_overall | 0.759048155 | 0.759048155 | 0.759048155 | 0.606593987 |
| amax_overall | 0.039849758 | 0.039849758 | 0.039849758 | 0.067426217 |
| amin_overall | -0.628700272 | -0.628700272 | -0.628700272 | -0.160408688 |

FIG. 11A

| TOUCH AND MOTION FEATURES | NORMALIZED VALUES USED WITH TOUCH SAMPLE #1 | NORMALIZED VALUES USED WITH TOUCH SAMPLE #2 | NORMALIZED VALUES USED WITH TOUCH SAMPLE #3 | LOGISTIC REGRESSION PARAMETER VALUE |
|---|---|---|---|---|
| mean_l2_norm | 1.371032629 | 1.371032629 | 1.371032629 | -0.284625723 |
| mean_l1_norm | 1.503128655 | 1.503128655 | 1.503128655 | -0.071550917 |
| root_mean_sq | 1.256978410 | 1.256978410 | 1.256978410 | 0.143942452 |
| curve_len | 0.053675119 | 0.053675119 | 0.053675119 | 0.077025616 |
| diff_entropy | 1.008601092 | 1.008601092 | 1.008601092 | 0.014043186 |
| energy | 0.670929916 | 0.670929916 | 0.670929916 | -0.078153174 |
| std_energy | 1.341722610 | 1.341722610 | 1.341722610 | -1.011351085 |
| peak_magnitude | 2.651186002 | 2.651186002 | 2.651186002 | 0.528717258 |
| peak_magnitude_frequency | -0.467271963 | -0.467271963 | -0.467271963 | 0.057121544 |
| peak_power | 2.768283719 | 2.768283719 | 2.768283719 | -0.497719085 |
| peak_power_frequency | -0.493053042 | -0.493053042 | -0.493053042 | -0.016200471 |
| magnitude_entropy | -1.843469771 | -1.843469771 | -1.843469771 | 0.042320057 |
| power_entropy | -1.951934514 | -1.951934514 | -1.951934514 | -0.019722869 |
| energy_%_btwn_3_and_7 | -0.188441288 | -0.188441288 | -0.188441288 | -0.042998277 |
| intercept | | | | -0.104890880 |

FIG. 11B $$\text{stress level value} = \frac{1}{1 + e^{(-t)}}$$

$$t = \left( \sum_{\text{feature}} \text{feature value} * \text{feature parameter} \right) + \text{intercept}$$

FIG. 12

DETERMINING A STRESS LEVEL OF A SMARTPHONE USER BASED ON THE USER'S TOUCH INTERACTIONS AND MOTION SENSOR DATA

TECHNICAL FIELD

The present invention relates to a method for determining the stress level of a person based only on how the person uses a smartphone by weighting contributions of both the person's touch interactions with the smartphone and movements of the smartphone as indicated by motion sensor data.

BACKGROUND

Stress is a significant health problem in modern-day life. In fact, many doctors argue that stress and stress-related symptoms are a major cause of death. Consequently, methods of measuring and monitoring stress can provide significant health benefits. A person comes under stress when that person's physical safety or emotional balance is threatened. In the short term, adrenalin is released, the person becomes tense, the person's heart rate and blood pressure increase, and other physiological systems prepare to meet the threat. When the threat passes, the person's body regains its normal equilibrium. However, extended activation of the body's stress response has a harmful effect on human health because the body is prevented from returning to its equilibrium state. Extended periods of increased heart rate, blood pressure, breathing rate and stress hormones harm the body's cardiovascular system, immune system and general metabolism, which can lead to hypertension, obesity and cognitive and emotional impairment.

In order to avoid the damage that chronic stress can cause, methods have been developed to reduce stress in one's work life and private life. Some treatments for relieving the physical symptoms of stress involve relaxation and meditation techniques guided by smartphone apps. These treatments are most effective, however, when the user receives feedback regarding how the relaxation and meditation techniques are influencing the user's physiological state. Moreover, it is preferable if the user need not acquire and carry dedicated sensors and wearables other than the smartphone itself that are required to measure parameters such as arterial pressure, electrocardiogram signals, respiratory volume or body temperature. Accordingly, a method is sought for accurately determining the stress levels of smartphone users who are undergoing stress reduction treatments that does not require input from sensors other than those present on standard smartphones.

SUMMARY

A method for determining a user's stress level is performed by a mobile app running on a smartphone. The method includes generating touch feature values and motion feature values, weighting the feature values by regression parameters, and generating a stress score for the user based on the weighted touch feature values and weighted motion feature values. The touch feature values indicate how the user's finger moves over the smartphone screen and are generated from touch data points including X positions, Y positions and associated touch timestamp values. The motion feature values indicate the movement of the smartphone and are generated from motion data points including X movements, Y movements, Z movements and associated motion timestamp values. The regression parameters are generated using touch and motion data identified by other users as being acquired while those other users were experiencing various perceived levels of stress. The app indicates to the user whether the stress score is higher or lower than a previously generated stress score.

A method for determining a stress score of the user of a smartphone is based on touch and motion data sensed by the smartphone and does not require inputs from wearable devices or other sensors. A computing system on the smartphone receives touch data points of the smartphone user that each includes an X position value, a Y position value and an associated touch timestamp value. The touch data points are segmented into discrete movements of the user's finger on the screen of the smartphone. The computing system receives motion data points of the smartphone that each includes an X movement value, a Y movement value, a Z movement value and an associated motion timestamp value. The motion data points are segmented into discrete time intervals including a first time interval. The first time interval is associated with those discrete movements of the user's finger that occur entirely within the first time interval.

Values of touch features are calculated for each discrete movement within the first time interval. Values of motion features associated with the first time interval are calculated. The touch features and the motion features are normalized based on prior touch data points and motion data points previously acquired while the user was using the smartphone. A stress level value is calculated for each discrete movement within the first time interval by applying logistic regression parameters to the normalized touch features and the normalized motion features. The logistic regression parameters are generated using a logistic regression model trained on touch data points and motion data points acquired from other users during time intervals identified by those other users as being associated with various levels of stress.

A stress score of the user during the first time interval is determined based on the stress level values of the discrete movements within the first time interval. An indication is displayed of how the stress score of the user has changed since the stress score of the user was last determined. The user is prompted to engage in a stress mitigation activity based on the determined stress score.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIGS. 5A and 5B are a table listing the components of forty-six exemplary touch data points.

FIGS. 6A, 6B, 6C, 6D, 6E, 6F, 6G, 6H and 6I are a table listing the components of 585 exemplary motion data points.

FIG. 7 is a table listing the values of thirty-two touch features for each of five touch samples as well as the mean and standard deviation of the touch features.

FIG. 8 shows the formula by which the value of the touch feature "distance_covered" is calculated.

FIG. 9 shows the formula by which the value of the touch feature "distance_spanned" is calculated.

FIG. 10 is a table listing the values of twenty-nine motion features for a motion sample as well as the mean and standard deviation of the motion features.

FIGS. 11A and 11B are a table listing the normalized touch and motion features associated with three touch samples as well as the regression parameter values associated with the touch and motion features.

FIG. 12 shows the formula by which the stress level value associated with a touch sample is calculated.

DETAILED DESCRIPTION

Reference will now be made in detail to some embodiments of the invention, examples of which are illustrated in the accompanying drawings.

Figure 1:
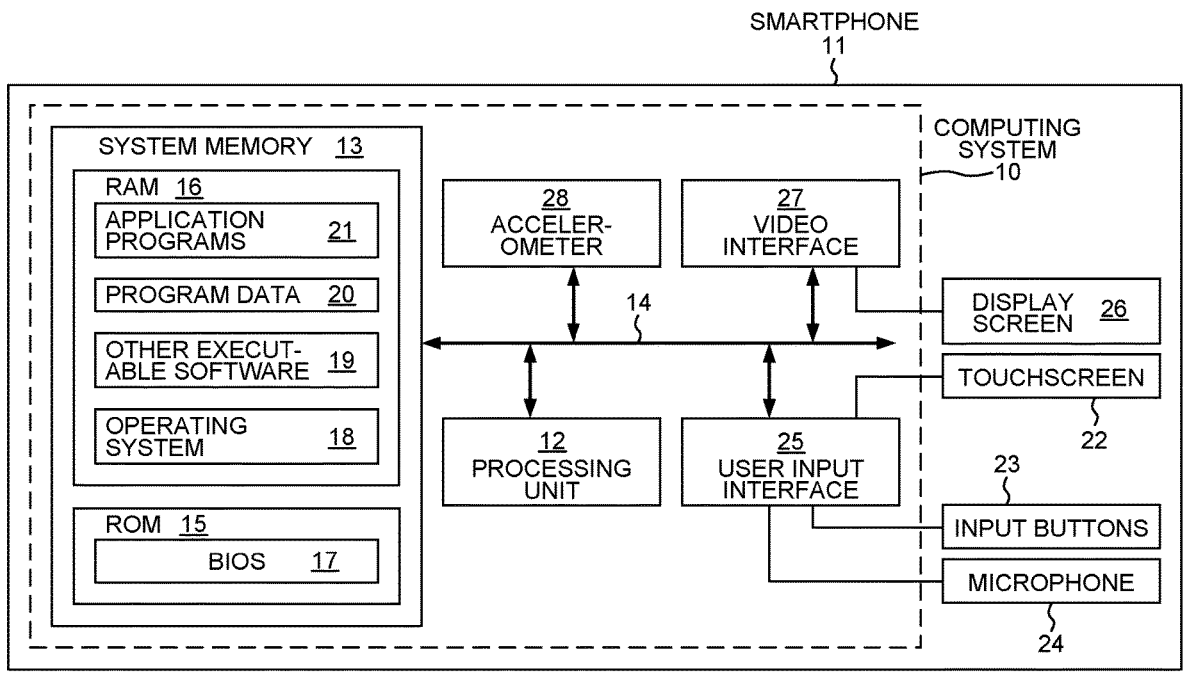
FIG. 1 is a schematic diagram of a computing system that runs a smartphone app.

FIG. 1 is a simplified schematic diagram of a computing system 10 on a smartphone 11, which is a mobile telecommunications device. System 10 can be used to implement a method for determining the stress level of a smartphone user based only on that person's touch interactions with the smartphone and the movements of the smartphone as measured by an accelerometer in the phone. Portions of the computing system 10 are implemented as software executing as a mobile App on the smartphone 11. Components of the computing system 10 include, but are not limited to, a processing unit 12, a system memory 13, and a system bus 14 that couples the various system components including the system memory 13 to the processing unit 12. Computing system 10 also includes computing machine-readable media used for storing computer readable instructions, data structures, other executable software and other data.

The system memory 13 includes computer storage media such as read only memory (ROM) 15 and random access memory (RAM) 16. A basic input/output system 17 (BIOS), containing the basic routines that transfer information between elements of computing system 10, is stored in ROM 15. RAM 16 contains software that is immediately accessible to processing unit 12. RAM includes portions of the operating system 18, other executable software 19, and program data 20. Application programs 21, including smartphone "apps", are also stored in RAM 16. Computing system 10 employs standardized interfaces through which different system components communicate. In particular, communication between apps and other software is effected through application programming interfaces (APIs), which define the conventions and protocols for initiating and servicing function calls.

A user of computing system 10 enters commands and information through input devices such as a touchscreen 22, input buttons 23 and a microphone 24. A display screen 26, which is physically combined with touchscreen 22, is connected via a video interface 27 to the system bus 14. Touchscreen 22 includes a contact intensity sensor, such as a piezoelectric force sensor, a capacitive force sensor, an electric force sensor or an optical force sensor. These input devices are connected to the processing unit 12 through a user input interface 25 that is coupled to the system bus 14. User input interface 25 detects the contact of a finger of the user with touchscreen 22. Interface 25 includes various software components for performing operations related to detecting contact with touchscreen 22, such as determining if contact (a fingerdown event) has occurred, determining the pressure of the contact, determining the size of the contact, determining if there is movement of the contact and tracking the movement across touchscreen 22, and determining if the contact has ceased (a finger-up event). User input interface 25 generates a series of touch data points, each of which includes an X position, a Y position, a touch pressure, a touch size (by minimum and maximum radius), and an associated touch timestamp value. The touch timestamp value indicates the time at which the X position, Y position, touch pressure and touch size where measured.

Computing system 10 also includes an accelerometer 28, whose output is connected to the system bus 14. Accelerometer 28 outputs motion data points indicative of the movement of smartphone 11. Each motion data point includes an X movement value, a Y movement value, a Z movement value and an associated motion timestamp value. The motion timestamp value indicates the time at which the X movement value, Y movement value and Z movement value were measured. In some embodiments, accelerometer 28 actually includes three accelerometers, one that measures X movement, one that measures Y movement, and one that measures Z movement. The wireless communication modules of smartphone 11 have been omitted from this description for brevity.

Figure 2:
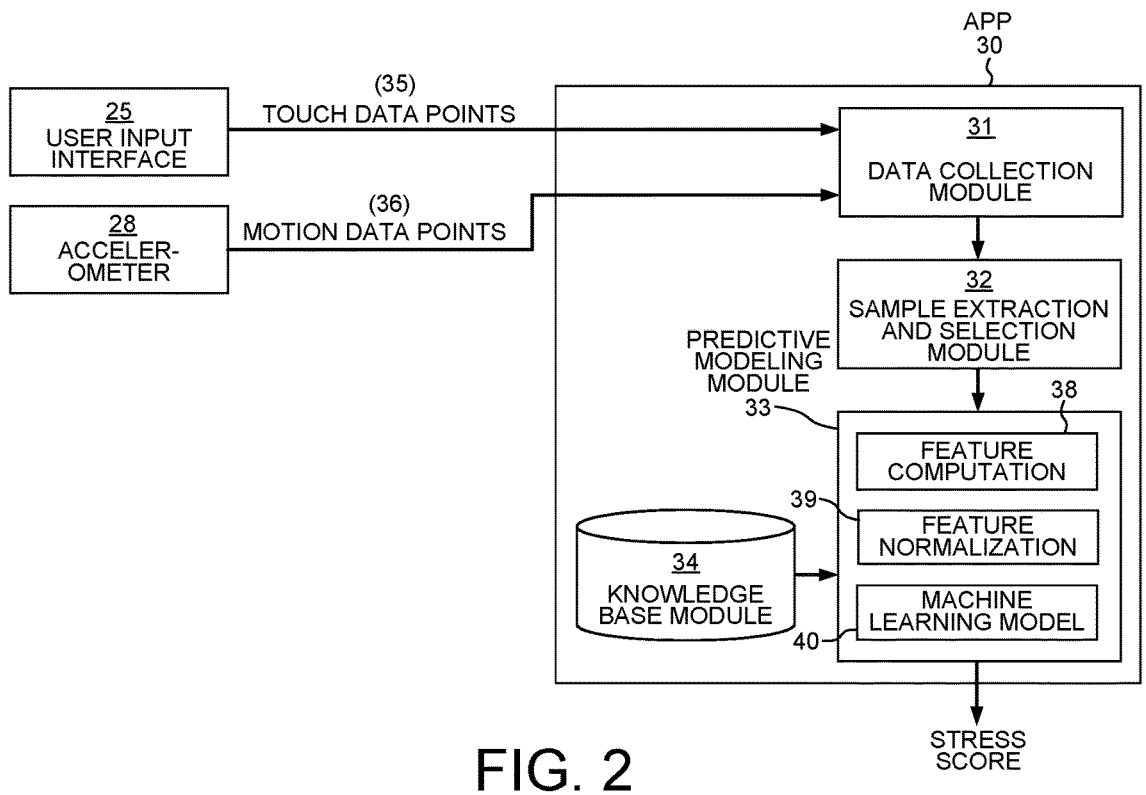
FIG. 2 is a schematic diagram of the components of the smartphone app that determines the stress level of the smartphone app user.

FIG. 2 is a schematic diagram of the components of one of the application programs 21 running on smartphone 11. This mobile application (app) 30 is part of computing system 10. App 30 includes a data collection module 31, a sample extraction and selection module 32, a predictive modeling module 33 and a knowledge base module 34. In one embodiment, mobile app 30 is one of the application programs 21. In another embodiment, at least some of the functionality of app 30 is implemented as part of the operating system 18 itself. For example, the functionality can be integrated into the iOS mobile operating system or the Android mobile operating system.

Data collection module 31 collects logs of user interactions with smartphone 11, both as touch interaction logs from user input interface 25 and as motion data from accelerometer 28. Software development kits (SDKs) specific to the operating system of smartphone 11 are used to enable data collection module 31 to collect the logs of the user's interactions with smartphone 11 and the motion sensor output. Thus, data collection module 31 collects data using layers of the operating system 18. However, in the embodiment in which app 30 is implemented entirely as a mobile app, only touch interaction data based on user interactions within the app itself can be collected. In the embodiment in which app 30 is implemented partly within the operating system 18, user interactions are collected independently of which app or screen of the smartphone is being used. In that case, for example, touch data generated on social networking, texting or chat apps can be collected. FIG. 2 shows that data collection module 31 collects touch data points 35 from user input interface 25 and motion data points 36 from accelerometer 28. In addition, data collection module 31 also collects reports in which users indicate their physiological and cognitive states.

Sample extraction and selection module 32 segments the continuous stream of touch data points 35 and motion data points 36 into discrete data samples and assesses whether the characteristics of the data of each sample warrant using the data in determining the user's stress. Module 32 parses the individual streams of interaction logs and motion data into a discrete series of samples. Module 32 separately extracts the samples from interaction logs and motion data.

Figure 3:
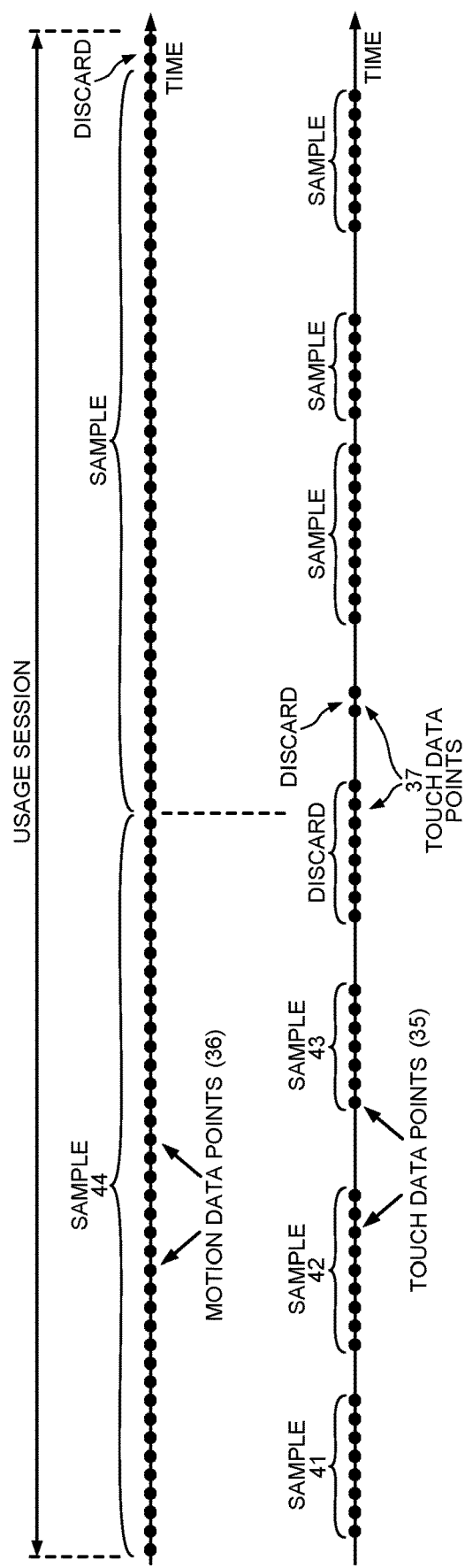
FIG. 3 illustrates motion data points segmented into evenly sized time intervals and touch data points segmented into discrete touch events.

The motion data points 36 of accelerometer data are segmented into evenly sized time intervals with a predefined time length starting from the first collected data point within a usage session, as illustrated in FIG. 3. The last (and shorter) interval of data in a usage session is discarded. For example, module 32 segments the continuous stream of motion data points 36 into discrete samples each having a length of twenty seconds. The last group of motion data points 36 in the usage session, which is nearly always shorter than twenty seconds, is discarded. In one scenario, the daily usage of a smartphone user is one usage session. Thus, in a two-week period, there would be fourteen usage sessions.

The touch data points 35 of interaction logs are segmented into discrete touch events separated by interruptions. The interruptions in the touch events are already designated in the output of the software development kits (SDKs) and are included as part of the touch interaction logs received by data collection module 31. Touch events whose time lengths do not fall within a predefined range (e.g., 0.1 sec to 5 sec) are not used as samples and are discarded. In addition, a touch event that does not fall entirely within a concurrent sample of motion data points 36, such as a 20-second period, is discarded. FIG. 3 illustrates touch data points 37 that are discarded either because the associated touch event does not fall entirely within a 20-second sample of motion data points 36 or because the touch event is too short.

Predictive modeling module 33 receives the segmented samples of motion data, including motion data points 36, and interaction logs, including touch data points 35, from sample extraction and selection module 32. Module 33 includes three components: a feature computation component 38, a feature normalization component 39, and a machine learning model 40. Feature computation component 38 computes motion features and touch features from the samples of motion and touch data that it receives in a raw format from module 32. Examples of motion features include the energy of the movement of the smartphone during a motion sample and the mean x movement per time increment during a motion sample. For example, the accelerometer determines the movement in the x dimension after each time increment of ten milliseconds. Examples of touch features include the speed, curvature and distance covered of a touch event, such as a swipe.

Feature normalization component 39 normalizes the motion features and touch features to each particular user. The magnitudes of the features are influenced in large part by usage patterns of individual users, which in turn depend on the type of device used. For example, the size and type of touchscreen 22 significantly influences the magnitudes of the features. Therefore, each of the many motion features and touch features is normalized based on the mean magnitude of that feature and the standard deviation of that feature for the particular user over a period of past use, such as a 2-week usage period. The user is assumed not to have changed the type of smartphone used during the normalization usage period.

Machine learning model 40 determines the user's physiological and cognitive states, such as the user's stress level, based on the normalized motion features, the normalized touch features, and a weight or parameter for each of the features calculated using machine learning on a knowledge base of features for which prior users have indicated their perceived stress levels during each usage session. The knowledge base is stored in knowledge base module 34. For example, in one implementation, the knowledge base was acquired from the usage patterns of 110 users each over fourteen daily usage sessions. For each usage session, sixty-one motion and touch features were calculated. The users indicated their perceived stress level on a scale between 0-10 for each usage session. Thus, there were 93,940 entries, each associated with a stress level between zero and ten. The entries were divided into two equal groups, half having higher associated stress levels and the other half having lower associated stress levels. Each of the 46,970 entries associated with lower stress were deemed to represent a no-stress state, and each of the other 46,970 entries associated with higher stress were deemed to represent a stress state. In one embodiment, the entries in knowledge base module 34 are fixed and immutable. In another embodiment, the knowledge base is periodically augmented with additional entries from users who rate their stress levels during each usage session. Thus, the augmented knowledge base grows over time.

Machine learning model 40 then performs a logistic regression on the 93,940 entries from knowledge base module 34 and calculates logistic regression parameters for each of the sixty-one motion and touch features. In this example implementation, the feature parameter with the highest correlation to the stress state is the standard deviation of the overall motion. The magnitude of the parameter std_overall is 0.701. The feature parameter with the highest correlation to the no-stress state is the standard deviation of the energy of the overall motion. The magnitude of the parameter std_energy is −1.011. Thus, a positive parameter correlates to more stress, and a negative parameter correlates to less stress. The magnitudes or weights of the parameters do not necessarily fall within any range, such as an arbitrary range between −1.0 and 1.0.

Machine learning model 40 then applies the parameters to each of the sixty-one motion and touch features associated with each touch sample (discrete touch event), and a stress level is determined for the touch sample. In this implementation, there are thirty-two touch features and twenty-nine motion features. The stress level is determined for a touch sample based not only on the touch features associated with the touch sample, but also on the motion features of the motion sample to which the touch feature corresponds. A touch sample corresponds to a motion sample if the touch data points 35 of the touch sample fall entirely within the period of the motion sample. In the example illustrated in FIG. 3, there are three touch samples 41-43 whose touch data points 35 fall entirely within the motion sample 44. In this example, machine learning model 40 determines a stress level for each of the three touch samples 41-43. Each determination is based on the thirty-two touch features of the corresponding touch sample as well as on the twenty-nine motion features of motion sample 44.

In one aspect, the stress levels determined for each of the three touch samples are averaged to obtain a stress level for the motion sample associated with a time interval of motion data. In this implementation, machine learning model 40 outputs a stress level associated with each 20-second motion sample. App 30 displays an indication on display screen 26 of how the stress level of the user has changed since the stress level was last determined by displaying a numerical representation of the determined stress level. Alternatively, App 30 displays an indication of how the stress level of the user has changed merely by indicating to the user whether the stress level is higher or lower than a previously determined stress level. For example, the size of a green arrow or dot could correspond to a decrease in the user's stress level, and a the size of a red arrow or dot could correspond to an increase in the user's stress level. Another alternative would be to indicate the user's measured stress level using non-verbal audio feedback, such as a higher or lower pitched tone.

Figure 4:
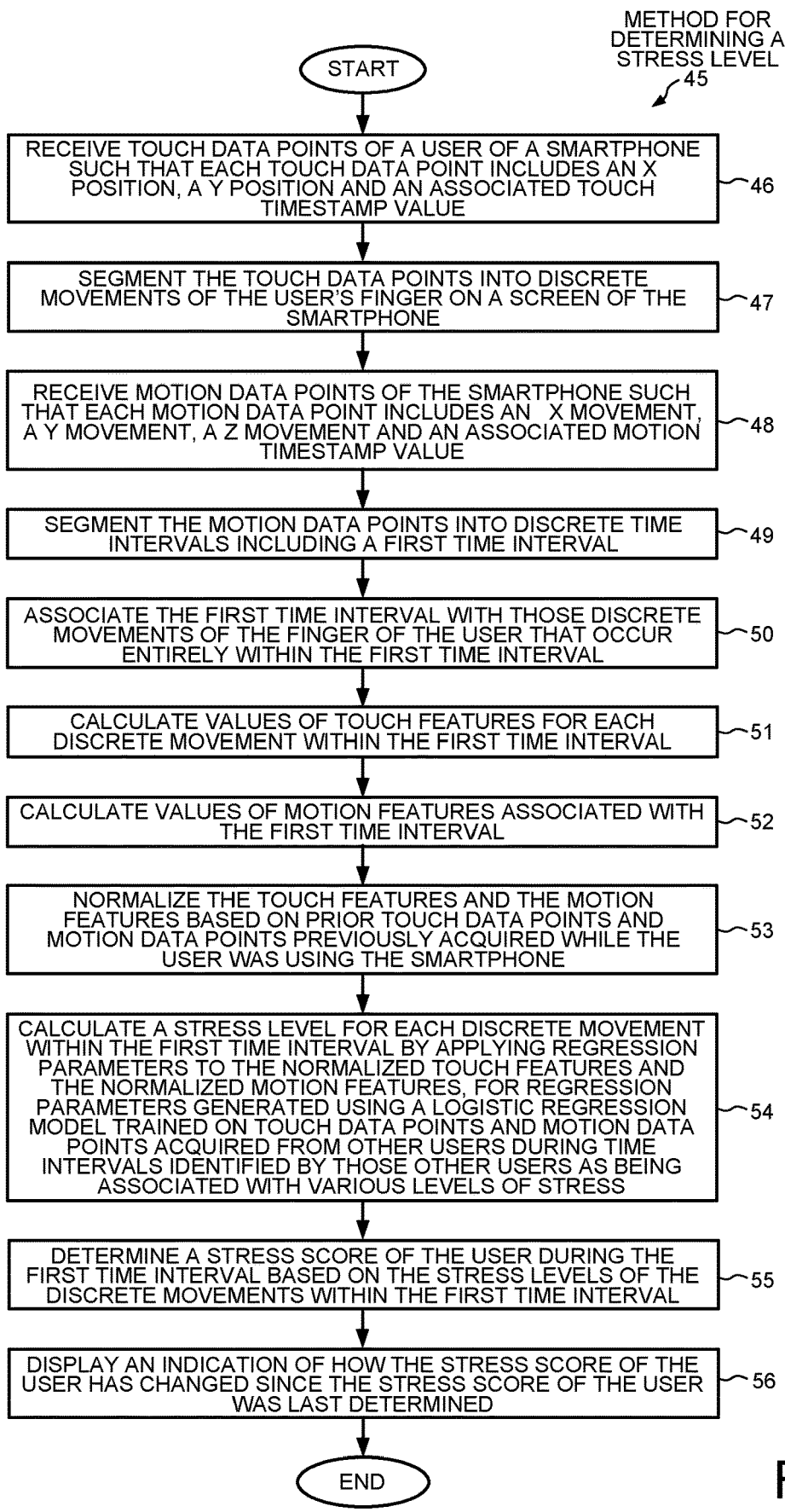
FIG. 4 is a flowchart of steps of a method by which the smartphone app uses touch and motion data to determine the current stress level of the user of the smartphone app.

FIG. 4 is a flowchart of steps 46-56 of a method 45 by which App 30 uses data sensed by smartphone 11 to determine the current stress level of the user of App 30. The steps of FIG. 4 are described in relation to App 30 and computing system 10 which implement method 45.

In step 46, data collection module 31 receives touch interaction data from smartphone 11 indicative of a user's interactions with touchscreen 22 of smartphone 11. The touch data is received as touch interaction logs based on data sensed by user input interface 25. The touch data comprises touch data points 35, each of which includes an X position value, a Y position value and an associated touch timestamp value.

FIGS. 5A-5B are a table listing forty-six exemplary touch data points 35. In addition to the X position value, Y position value and associated touch timestamp value, each point also includes values indicating the change in the X position (delta x), the change in the Y position (delta y), the pressure of the user's finger on touchscreen 22, the overall size of the touch impression on the screen, the minimum radius of the touch impression, the maximum radius of the touch impression and the orientation of the touch impression. In the exemplary touch data points 35, the size value has not been sensed, and is listed as zero. The timestamp values are listed in units of milliseconds.

In step 47, sample extraction and selection module 32 segments the continuous stream of touch data points 35 into discrete data samples representing distinct movements of the user's finger on touchscreen 22. If the values for both delta x and delta y are zero for a particular timestamp value, then the touch event of the user's finger has stopped, and a new touch event is deemed to have begun. Each touch event is analyzed as a separate sample. In FIGS. 5A-5B, for example, the delta x and delta y values are both zero at touch data points 14, 22, 30 and 38. Thus, a first touch event sample #1 includes touch data points 1-14, sample #2 includes points 15-22, sample #3 includes points 23-30, sample #4 includes points 31-38 and sample #5 includes points 39-46.

In step 48, data collection module 31 receives motion sensor data from smartphone 11 indicative of the movement of the smartphone while the user's finger is moving over touchscreen 22 of smartphone 11. At least a portion of the sensed movement of smartphone 11 associated with the motion data has occurred concurrently with the user's interactions with touchscreen 22. The motion sensor data comprises motion data points 36, each of which includes an X movement value, a Y movement value, a Z movement value and an associated motion timestamp value. The motion timestamp value indicates the time at which the X movement value, Y movement value and Z movement value were measured by accelerometer 28.

FIGS. 6A-6I are a table listing 585 exemplary motion data points 36. The timestamp values are listed in units of milliseconds. The table also lists the total time elapsed in seconds since the first motion data point was measured. FIGS. 6A-6I include 5.855 seconds of motion data. In FIG. 3, the example usage session was segmented into 20-second samples of motion data points 36. The last motion sample that was shorter than twenty seconds in length was discarded. To reduce the amount of data in this example, the 585 motion data points 36 of FIGS. 6A-6I are segmented into motion samples of no more than five seconds.

In step 49, the motion data points 36 of accelerometer data are segmented into evenly sized time intervals with a predefined time length (5 seconds) starting from the first collected data point within the usage session. In this example, the first time interval includes motion data points 1-499. The motion data points 500-585 are discarded because they include less than five seconds of data.

In step 50, the first time interval of motion data points 36 (motion sample #1) is associated with those discrete movements of the user's finger that occur entirely within the first time interval. A touch sample is associated with a motion sample if the touch data points 35 of the touch sample fall entirely within the period of the motion sample. In the example illustrated in FIG. 3, there are three touch samples 41-43 whose touch data points 35 fall entirely within the motion sample 44. Of the five touch samples included in FIGS. 5A-5B, only touch samples #1-#3 have touch data points with touch timestamp values that fall entirely within the motion timestamp values of motion sample #1 of FIGS. 6A-6I.

FIG. 6C shows the highlighted motion timestamp values of motion data points 160-177 within motion sample #1, which coincide with the touch timestamp values of touch data points 1-14 of touch sample #1 of FIG. 5A. Touch sample #1 runs from timestamp 1583005689576 to timestamp 1583005689753. FIGS. 6D-6E show the highlighted motion timestamp values of motion data points 277-291 within motion sample #1, which coincide with the touch timestamp values of touch data points 15-22 of touch sample #2 of FIG. 5A. Touch sample #2 runs from timestamp 1583005690747 to timestamp 1583005690903. FIG. 6F shows the highlighted motion timestamp values of motion data points 410-418 within motion sample #1, which coincide with the touch timestamp values of touch data points 23-30 of touch sample #3 of FIG. 5A. Touch sample #3 runs from timestamp 1583005692082 to timestamp 1583005692170. However, the touch timestamp values of touch data points 31-38 of touch sample #4 of FIG. 5B coincide with the highlighted motion timestamp values of motion data points 517-524, which occur after the end of motion sample #1 at motion data point 499. Thus, touch sample #4 is not associated with motion sample #1, and the touch data points 35 of touch sample #4 are not used to calculate features in method 45. Similarly, the touch timestamp values of touch data points 39-46 of touch sample #5 of FIG. 5B coincide with the highlighted motion timestamp values of motion data points 578-585, which occur after the end of motion sample #1 at motion data point 499. Thus, touch sample #5 is also not associated with motion sample #1, and the touch data points 35 of touch sample #5 are not used to calculate features in method 45. Although in the exemplary touch data of FIGS. 5A-5B there are no touch samples whose time lengths are less than a predefined threshold (e.g., 0.05 sec), any such short samples would also be discarded and not used to calculate features in method 45.

In step 51, feature computation component 38 of predictive modeling module 33 calculates the values of touch features for each discrete movement within the first time interval. In this example, thirty-two touch features are calculated for each of touch samples #1-#3 which fall within motion sample #1. The touch features are calculated using the touch data points 35 listed in FIGS. 5A-5B. FIG. 7 is a table listing the values of the thirty-two touch features for each of touch samples #1-#5. Only the feature values are samples #1-#3 are used in further calculations. The thirty-two touch features include: distance_covered, distance_spanned, efficiency, duration, speed, num_points, curvature, pressure_median, pressure_mean, pressure_std, pressure_max, pressure_min, radiusMin_median, radiusMin_mean, radiusMin_std, radiusMin_max, radiusMin_min, radiusMax_median, radiusMax_mean, radiusMax_std, radiusMax_max, radiusMax_min, orientation_median, orientation_mean, orientation_std, orientation_max, orientation_min, size_median, size_mean, size_std, size_max, and size_min.

The distance_covered is the entire distance_covered by the user's finger during a touch event, whereas the distance_spanned is the straight-line distance between the beginning and the end of the touch event. FIG. 8 shows how the touch feature "distance_covered" is calculated for touch sample #1 using the touch data points 1-14. The sum of the distances between the xy positions at the end of each touch data point is calculated using the delta_x and delta_y values for touch data points 1-14 in FIG. 5A. The result is 200.3943288, which is listed as the touch feature value for distance_covered for touch sample #1 in FIG. 7.

FIG. 9 shows how the touch feature "distance_spanned" is calculated for touch sample #1 using the first touch data point 1 of sample #1 and the first touch data point 14 of touch sample #2. The distances between the xy position at the beginning of touch sample #1 and the xy position at the beginning of touch sample #2 is calculated using the x_position and y_position values for touch data points 1 and 14 in FIG. 5A. The result is 195.0025641, which is listed as the touch feature value for distance_spanned for touch sample #1 in FIG. 7.

The touch feature "efficiency" is calculated as the ratio of distance_spanned to distance_covered. For the touch sample #1, the efficiency is 195.0025641/200.3943288, which equals 0.973094225 as listed in FIG. 7. The touch feature "duration" is an indication of the duration of a swipe of the user's finger over screen 26 of smartphone 11. The feature "duration" is calculated as the difference between the final and initial timestamps of the touch sample. For the touch sample #1, the duration is (1583005689753−1583005689576), which equals 177 milliseconds. The duration is listed in FIG. 7 as 0.177 seconds. The feature "pressure_mean" is an indication of the average pressure applied by the user's finger to screen 26 of smartphone 11 during a swipe or touch event.

In step 52, feature computation component 38 calculates the values of motion features associated with the first time interval. The values of the motion features are determined using motion data points 36 listed in FIGS. 6A-6I whose timestamps fall within motion sample #1. In this example, twenty-nine motion features are calculated for motion sample #1. FIG. 10 is a table listing the values of the twenty-nine motion features, which are: mean_x, std_x, var_x, mean_y, std_y, var_y, mean_z, std_z, var_z, mean_overall, median_overall, std_overall, var_overall, amax_overall, amin_overall, mean_l2_norm, mean_l1_norm, root_mean_sq, curve_len, diff_entropy, energy, std_energy, peak_magnitude, peak_magnitude frequency, peak_power, peak_power_frequency, magnitude_entropy, power_entropy, and energy_pct_between_3_and_7.

In step 53, feature normalization component 39 of predictive modeling module 33 normalizes the touch features and the motion features based on prior touch data points 35 and motion data points 36 previously acquired while the user was using smartphone 11. The touch and motion features are normalized using the past mean of each feature and the past standard deviation of each feature for the particular user. In one implementation, touch and motion data is acquired for the user over a 2-week period, and then the mean value and the standard deviation of each touch and motion feature are determined. Note that the user must be using the same smartphone 11 over the entire 2-week period because the feature values are heavily influenced by screen size and other characteristics that vary for different smartphones. FIG. 7 lists the mean and the standard deviation for each touch feature for the particular user in the last two columns. FIG. 10 lists the mean and the standard deviation for each motion feature for the particular user in the last two columns. FIGS. 11A-11B list the normalized touch and motion features associated with touch samples #1-#3.

The normalized value for each feature is calculated as the difference between the feature value and the feature mean, with the difference then divided by the standard deviation of the feature. For example, the normalized distance_covered for touch sample #1 is calculated as (200.3943288−196.713947)/48.93410519, which equals 0.075210975. The inputs are listed in the first row of FIG. 7, and the normalized distance_covered is listed in the first row of FIG. 11A. Note that the same normalized motion feature values are used with each of the three distinct touch feature values for touch samples #1-#3, as shown in the columns of FIGS. 11A-11B. Thus, in the ultimate determination of the stress level associated with each touch sample, the contribution of the motion features is the same.

In step 54, the machine learning model 40 of predictive modeling module 33 determines a stress level value for each of the three touch samples #1-#3. Each determination is based on both the thirty-two touch features of the corresponding touch sample and the twenty-nine motion features of motion sample #1. A stress level value is generated for each discrete movement within the first time interval of motion sample #1 by applying logistic regression parameters to weight each of the normalized touch and motion features. The values of the sixty-one logistic regression parameters associated with each touch and motion feature are listed in the last column of FIGS. 11A-11B. The stress level value of each touch sample is calculated using the formula of FIG. 12. The value of "t" in the formula is the sum of the products of the sixty-one feature values times their associated regression parameters; an intercept value is then added to the sum. The calculated stress level value falls within a range of zero to one, in which one represents the maximum possible stress.

For this exemplary touch and motion data, the sums of the products of the sixty-one feature values times their associated regression parameters for the touch samples #1, #2 and #3 are −0.861821372, −0.952629425 and −0.975875892, respectively. The resulting stress levels for touch samples #1, #2 and #3 are 0.275536305, 0.257783613 and 0.25336094, respectively The regression parameters used in step 54 are generated using a logistic regression model trained on touch data points and motion data points acquired from other users during time intervals identified by those other users as being associated with various levels of stress. In this example, the touch and motion data was acquired from 110 other users over fourteen daily usage sessions. The users recorded their perceived stress level on a scale between 0-10 for each usage session. Thus, each touch data point and motion data point is associated with a stress level value corresponding to that of the usage session during which the data was acquired. The data from the usage sessions is divided into a first half with the highest stress rankings and a second half with the lowest stress rankings. The data in the first half is deemed to be associated with a stress level of one, and the data in the second half is deemed to be associated with a stress level of zero. Thirty-two touch features and the twenty-nine motion features are then calculated for each usage session. Machine learning in the form of logistic regression is used to determine the relative contribution of each of the sixty-one features to the perceived stress level of the usage session being one or zero. The magnitudes of the relative contribution are expressed by the logistic regression parameter values listed in the last column of FIGS. 11A-11B. These values are stored in knowledge base module 34.

For this sample knowledge base, the feature with the greatest correlation to the user's stress level is the standard deviation of energy of the motion data points (std_energy), which has a negative contribution to stress of −1.011. The feature with the biggest positive correlation to the user's stress level is the overall standard deviation of the motion data points (std_overall), which has a positive contribution to stress of 0.701. Another motion feature with a large contribution to the user's stress level is the peak magnitude of the motion data points while the user's finger moves over the screen, which has a positive contribution to stress of 0.529.

Touch features that make a large contribution to the user's stress level are the minimum size of the touch (size_min), the standard deviation of the touch size (size_std) and the minimum of the radius of the minimum sized touches (radiusMin_min). For this sample knowledge base, the resulting regression parameters result in an overall contribution to the stress level by the motion features of about 78% and an overall contribution to the stress level by the touch features of about 22%. However, the accuracy of the overall stress level determination is improved by using both motion features and touch features in a combined weighted model to determine the stress level of the user.

In step 55, a stress score of the user during the first time interval is determined based on the stress level values calculated for the discrete touch movements during the first time interval. In this example, a stress score is calculated by averaging the determined stress level values of the touch samples #1-#3 that fall within the first time interval between the timestamps for motion data points 1 and 499. Thus, the stress score for motion sample #1 is 0.262, which is the average of the stress level values of the touch samples #1-#3. Note, however, that both the stress level values and the stress score are influenced by both the touch data points and the motion data points that occur during the first time interval.

In another embodiment, the stress score is determined to be the highest stress level value calculated for a touch sample during the first time interval. In yet another embodiment, stress level values are calculated for the touch samples (discrete finger movements) that occur during many motion samples acquired over longer periods of use of smartphone 11, such as a work day or portions of a day. The calculated stress level values are then averaged to determine a stress score for the day or portion of a day.

In step 56, an indication is displayed on screen 26 of how the stress score of the user has changed since the stress score was last determined. For example, an image is displayed indicating to the user that the stress score is higher or lower than a previously generated stress score. A numerical representation of the stress score is displayed on display screen 26 of smartphone 11. In another aspect, App 30 gives the user non-verbal audio feedback indicating to the user whether the stress score is higher or lower than the previously generated stress score. For example, a higher tone indicates a rising stress score, and a lower tone indicates a falling stress score.

In an alternative embodiment, instead of indicating in step 56 that the user's stress score has risen or fallen, the user is prompted to engage in an activity based on the determined stress score that is not indicated to the user. For example, App 30 prompts the user to engage in an intervention that is selected based on the determined stress score. If the user's stress score is above a predetermined threshold, the user is prompted to engage in relaxation and meditation techniques guided by App 30.

In one implementation of App 30, a company may recommend that its employees use the mobile app running on their smartphones to assist them in engaging in stress reduction techniques during the work day. Each employee's stress level is determined in the background as the employee uses the smartphone throughout the day without the employee having to perform any specific diagnostic procedures to measure his or her current stress level. If the employee's stress level exceeds a predetermined threshold, then App 30 notifies the employee and recommends a stress reduction activity, for example, meditation.

An advantage of method 45 for determining a stress level using App 30 on smartphone 11 is that the method does not require other sensors or wearable devices to determine the user's stress level. Over forty percent of the world's population owns a mobile device on which method 45 can be implemented, and most of these people use the mobile device regularly throughout the day. This ubiquity of mobile devices allows the method to be used by many more people than would otherwise be possible if purchasing a wearable device or medical-grade device were required to determine the user's stress level.

Another advantage of method 45 is that the user is not required to engage in any specific behavior during which the user's stress level is measured. Most other methods of determining a user's stress level require the user to adjust his or her patterns of behavior and to act in a way that the user would not otherwise act. However, method 45 is completely unobtrusive because the user's stress level is determined based on the user's normal usage of the mobile device or smartphone. Thus, the user of App 30 is more likely to engage in stress reduction techniques because the reluctance to perform additional steps to measure the user's current stress level is removed as an excuse for failing to implement the techniques.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
   generating a touch feature value from touch data points of a smartphone, wherein each touch data point includes an X position, a Y position and an associated touch timestamp value, and wherein the touch feature value is an indication of how a finger of a user moves over a screen of the smartphone;
   generating a motion feature value from motion data points of the smartphone, wherein each motion data point includes an X movement, a Y movement, a Z movement and an associated motion timestamp value, and wherein the motion feature value is an indication of movement of the smartphone including while the finger of the user moves over the screen of the smartphone;

segmenting the motion data points into non-overlapping time intervals, wherein at least a portion of a first time interval occurs concurrently with the touch data points as the finger of the user moves over the screen of the smartphone, and wherein the touch feature value is generated from the touch data points that fall within the first time interval;

weighting the touch feature value and the motion feature value by corresponding regression parameters, wherein the regression parameters are generated using a logistic regression model trained on touch data points and motion data points identified by other users as being acquired while those other users were experiencing various perceived levels of stress;

generating a stress score based on the weighted touch feature value and the weighted motion feature value; and indicating to the user whether the stress score is higher or lower than a previously generated stress score.

2. The method of claim 1, wherein the touch feature value is an indication of a duration of a swipe of the finger of the user over the screen of the smartphone.

3. The method of claim 1, wherein the touch feature is an indication of a pressure applied by the finger of the user to the screen of the smartphone.

4. The method of claim 1, wherein the motion feature value is an indication of standard deviation of the motion data points.

5. The method of claim 1, wherein the motion feature value is an indication of a peak magnitude of the motion data points while the finger of the user moves over the screen of the smartphone.

6. The method of claim 1, further comprising:
normalizing the touch feature value based on prior touch feature values acquired from prior movements of the finger of the user over the screen of the smartphone, wherein the weighting of the touch feature value is a weighting of the normalized touch feature value; and
normalizing the motion feature value based on prior movement of the smartphone that occurred concurrently while the user was using the smartphone, wherein the weighting of the motion feature value is a weighting of the normalized motion feature value, and wherein the generating of the stress score is based on the weighted normalized touch feature value and the weighted normalized motion feature value.

7. The method of claim 1, wherein the indicating to the user whether the stress score is higher or lower than the previously generated stress score involves non-verbal audio feedback.

8. The method of claim 1, further comprising:
prompting the user to engage in an activity based on the stress score.

9. A method comprising:
receiving touch data points of a user of a smartphone, wherein each touch data point includes an X position value, a Y position value and an associated touch timestamp value;

segmenting the touch data points into discrete movements of a finger of the user on a screen of the smartphone;

receiving motion data points of the smartphone, wherein each motion data point includes an X movement value, a Y movement value, a Z movement value and an associated motion timestamp value;

segmenting the motion data points into non-overlapping time intervals, wherein at least a portion of a first time interval occurs concurrently with the touch data points as the finger of the user moves over the screen of the smartphone, and wherein values of touch features are generated from the touch data points that fall within the first time interval;

associating the first time interval with those discrete movements of the finger of the user that occur entirely within the first time interval;

calculating the values of touch features for each discrete movement within the first time interval;

calculating values of motion features associated with the first time interval;

normalizing the touch features and the motion features based on prior touch data points and motion data points previously acquired while the user was using the smartphone;

calculating a stress level value for each discrete movement within the first time interval by applying regression parameters to the normalized touch features and the normalized motion features, wherein the regression parameters are generated using a logistic regression model trained on touch data points and motion data points acquired from other users during time intervals identified by those other users as being associated with various levels of stress;

determining a stress score of the user during the first time interval based on the stress level values of the discrete movements within the first time interval; and displaying an indication of how the stress score of the user has changed since the stress score of the user was last determined.

10. The method of claim 9, wherein the displaying an indication of how the stress score of the user has changed involves displaying a numerical representation of the determined stress score on the screen of the smartphone.

11. The method of claim 9, further comprising:
prompting the user to engage in an intervention, wherein the intervention is selected based on the determined stress score.

12. The method of claim 9, wherein one of the values of touch features is a touch pressure value.

13. The method of claim 9, wherein each touch data point includes a touch pressure value corresponding to the associated touch timestamp value.

14. The method of claim 9, wherein the normalizing is performed using mean values of the touch features generated using the prior touch data points previously acquired while the user was using the smartphone.

15. The method of claim 9, wherein the normalizing is performed using standard deviation values of the touch features generated using the prior touch data points previously acquired while the user was using the smartphone.

* * * * *